United States Patent [19]

Short

[11] Patent Number: 5,830,696
[45] Date of Patent: Nov. 3, 1998

[54] DIRECTED EVOLUTION OF THERMOPHILIC ENZYMES

[75] Inventor: Jay M. Short, Encinitas, Calif.

[73] Assignee: Diversa Corporation, San Diego, Calif.

[21] Appl. No.: 760,489

[22] Filed: Dec. 5, 1996

[51] Int. Cl.⁶ .............................. C12P 21/06; C07K 1/00
[52] U.S. Cl. ........................................ 435/69.1; 530/350
[58] Field of Search ............................ 435/69.1; 530/350

[56] References Cited

U.S. PATENT DOCUMENTS 5,352,778  10/1994  Comb et al. ........................... 536/23.2
5,500,363   3/1996  Comb et al. ........................... 435/194

*Primary Examiner*—Ponnathapura Achutamurthy
*Assistant Examiner*—Hankyel T. Park
*Attorney, Agent, or Firm*—Fish & Richardson P.C.

[57] ABSTRACT

Thermostable enzyme are subjected to mutagenesis to produce a thermophilic enzyme which is stable at thermophilic temperature and which has increased activities at least two-fold higher than the activity of the wild-type thermostable enzyme at lower temperatures, which are temperatures of 50° C. or lower.

2 Claims, 3 Drawing Sheets

FIG. 1A

```
1    ATG CTA CCA GAA GGC TTT CTC TGG GGC GTG TCC CAG TTC GAG ATG GGC    60
1    Met Leu Pro Glu Gly Phe Leu Trp Gly Val Ser Gln Phe Glu Met Gly    20

61   GAC AAG CTC AGG AGG AAC ATT GAT CCG AAC ACA GAC TGG AGG GTC CCC   120
21   Asp Lys Leu Arg Arg Asn Ile Asp Pro Asn Thr Asp Trp Lys Trp Val Arg Asp Pro   40

121  TTC AAC ATA AAG AGG GAA CTC GTC AGC GGC GAC CTG CCC GAG GAG ATA AAC AAC TAC   180
41   Phe Asn Ile Lys Arg Glu Leu Val Ser Gly Asp Leu Pro Glu Glu Gly Ile Asn Asn Tyr   60

181  GAA CTT TAC GAG AAG GAT CAC CCC CTC GCC AGA GAC CTG AAC GTT TAC CTG AAC GTT GAA   240
61   Glu Leu Tyr Glu Lys Asp His Pro Leu Ala Arg Asp Leu Asn Val Tyr Arg Ile   80

241  GGA ATA GAG TGG AGC AGG ATC TTT CCC TGG CCA ACC TGG TTT GTG GAG GTT GAC GTC CTC   300
81   Gly Ile Glu Trp Ser Arg Ile Phe Pro Trp Pro Thr Trp Phe Val Glu Val Asp Leu Glu   100

301  CGG GAC AGC TAC GGA CTC GTG AAG GAC GTC AAA ATC GAT AAA GAC ACG CTC GAA GAG CTC   360
101  Arg Asp Ser Tyr Gly Leu Val Lys Asp Val Lys Ile Asp Lys Asp Thr Leu Glu Glu Leu   120

361  GAC GAG ATA GCG AAT CAT CAG GAG ATA GCC TAC CGC GTT ATA GAG CAC CTC AGG   420
121  Asp Glu Ile Ala Asn His Gln Glu Ile Ala Tyr Tyr Arg Arg Val Ile Glu His Leu Arg   140

421  GAG CTG GGC TTC AAG GTC ATC GTC AAC CTC AAC CTC ACG CTC CCC CTC TGG CTT CAC   480
141  Glu Leu Gly Phe Lys Val Ile Val Asn Leu Asn His Phe Thr Leu Pro Leu Trp Leu His   160

481  GAT CCG ATA ATC GCG AGG GAG AAG GCC CTC ACC AAC GGT AGG ATT GGC TGG GTC GGG CAG   540
161  Asp Pro Ile Ile Ala Arg Glu Lys Ala Leu Thr Asn Gly Arg Ile Gly Trp Val Gly Gln   180
```

```
541  GAG AGC GTG GTG GAG TTC GCC AAG TAC ATC GCG AAC GCA CTC GGG GAC CTC   600
181  Glu Ser Val Val Glu Phe Ala Lys Tyr Ile Ala Asn Ala Leu Gly Asp Leu   200

601  GTT GAT ATG TGG AGC ACC TTC AAC GAR CCG ATG GTC GTT GAN CTC GGT CTC GCG   660
201  Val Asp Met Trp Ser Thr Phe Asn Glu Pro Met Val Val Xxx Leu Gly Tyr Leu Ala   220

661  CCC TAC TCC GGY TTT CCN CCG GGG GTT ATG AAC CCC GAG GCG GMN AAN CTG GCA ATC CTC   720
221  Pro Tyr Ser Gly Phe Pro Pro Gly Val Met Asn Pro Glu Ala Xxx Xxx Leu Ala Ile Leu   240

721  AAC ATA AAC GCC CAC GCA CTG GCC TAC AAG ATG ATA AAG TTC AAG TTC GAC AGG GTA AAG   780
241  Asn Met Ile Asn Ala His Ala Leu Ala Tyr Lys Met Ile Lys Phe Asp Arg Val Lys   260

781  GCC GAT AAG GAT TCC CGC TCC GAG GCC GGC GTC GAG ATA ATC TAC AAC AAC ATA GGC GTT   840
261  Ala Asp Lys Asp Ser Arg Ser Glu Ala Glu Val Gly Ile Ile Tyr Asn Asn Ile Gly Val   280

841  NCC TAT CCA NAC GAC TCC AAC GAC GTG AAA NCT NCA GAA AAC TAC   900
281  Xxx Tyr Pro Xxx Asp Ser Asn Asp Val Lys Xxx Xxx Glu Asn Tyr   300

901  TTC CAC AGC GGG CTC TTC TTC GAC GCA ATC CAC AAG GGG AAC GAC CTC AAC ATC GAG TTC GAC   960
301  Phe His Ser Gly Leu Phe Phe Asp Ala Ile His Lys Gly Asn Asp Leu Asn Ile Glu Phe Asp   320

961  GGT GAG ACC TTC GTC AAA GTT CGG CAT CTC AGG GGG AAC GAC TGG ATA GGC GTT AAC TAC   1020
321  Gly Glu Thr Phe Val Lys Val Arg His Leu Arg Gly Asn Asp Trp Ile Gly Val Asn Tyr   340

1021 TAC ACG AGA GAA GTC GTC AGG TAT TCG GAG CCC AAG TTC CCG AGC ATA CCC CTG ATA TCC   1080
341  Tyr Thr Arg Glu Val Val Arg Tyr Ser Glu Pro Lys Phe Pro Ser Ile Pro Leu Ile Ser   360
```

FIG. 1B

| 1081 | TTC | CGG | GGA | GTT | CAC | AAC | TAC | GGT | TGC | AGG | CCC | GGG | AGT | TCT | TCC | GCC | GAC | GGA | 1140 |
| --- | --- | --- | --- | --- | --- | --- | --- | --- | --- | --- | --- | --- | --- | --- | --- | --- | --- | --- | --- |
| 361 | Phe | Arg | Gly | Val | His | Asn | Tyr | Gly | Cys | Arg | Pro | Gly | Ser | Ser | Ser | Ala | Asp | Gly | 380 |
| 1141 | AGG | CCC | GTA | AGC | GAC | ATC | GGC | TGG | GAG | ATC | TAT | CCG | GAG | GGG | ATC | TAC | GAC | TCG | ATA | AGA | 1200 |
| 381 | Arg | Pro | Val | Ser | Asp | Ile | Gly | Trp | Glu | Ile | Tyr | Pro | Glu | Gly | Ile | Tyr | Asp | Ser | Ile | Arg | 400 |
| 1201 | GAG | GCC | AAC | AAA | TAC | GGG | GTC | CCG | GTT | TAC | GTC | ACC | GAA | AAC | GGA | ATA | GCC | GAT | TCA | ACT | 1260 |
| 401 | Glu | Ala | Asn | Lys | Tyr | Gly | Val | Pro | Val | Tyr | Val | Thr | Glu | Asn | Gly | Ile | Ala | Asp | Ser | Thr | 420 |
| 1261 | GAC | ACC | CTG | CGG | CCG | TAC | TAC | CTC | GCG | AGC | CAT | GTA | GCG | AAG | ATT | GAG | GAG | GCG | TAC | GAG | 1320 |
| 421 | Asp | Thr | Leu | Arg | Pro | Tyr | Tyr | Leu | Ala | Ser | His | Val | Ala | Lys | Ile | Glu | Glu | Ala | Tyr | Glu | 440 |
| 1321 | GCG | GGT | TAC | GAC | GTC | AGG | GGC | TAC | CTC | TAC | TGG | GCG | CTG | ACC | GAC | AAC | TAC | GAG | TGG | GCC | 1380 |
| 441 | Ala | Gly | Tyr | Asp | Val | Arg | Gly | Tyr | Leu | Tyr | Trp | Ala | Leu | Thr | Asp | Asn | Tyr | Glu | Trp | Ala | 460 |
| 1381 | CTC | GGT | TTC | AGG | ATG | AGG | TTC | GGC | CTC | TAT | AAA | GTG | GAT | CTC | ATA | ACC | AAG | GAG | AGA | ACA | 1440 |
| 461 | Leu | Gly | Phe | Arg | Met | Arg | Phe | Gly | Leu | Tyr | Lys | Val | Asp | Leu | Ile | Thr | Lys | Glu | Arg | Thr | 480 |
| 1441 | CCG | CGG | GAG | GAA | AGC | GTA | AAG | GTT | TAT | AGG | GGC | ATC | GTG | GAG | AAC | AAC | GGA | GTG | AGC | AAG | 1500 |
| 481 | Pro | Arg | Glu | Glu | Ser | Val | Lys | Val | Tyr | Arg | Gly | Ile | Val | Glu | Asn | Asn | Gly | Val | Ser | Lys | 500 |
| 1501 | GAA | ATC | CGG | GAG | AAG | TTC | GGA | CTT | GGG | TGA | 1530 |
| 501 | Glu | Ile | Arg | Glu | Lys | Phe | Gly | Leu | Gly | End | 510 |

FIG. 1C

DIRECTED EVOLUTION OF THERMOPHILIC ENZYMES

The present invention relates to enzymes, particularly to thermostable enzymes. More particularly, the present invention relates to thermostable enzymes which are stable at high temperature and which have improved activity at lower temperatures.

Thermostable enzymes are enzymes that function at greater than 60° C. Thermostable enzymes are utilized in both industry and biomedical research in assays where certain steps of the assay are performed at significantly increased temperatures. Thermostable enzymes may be obtained from thermophilic organisms found in hot springs, volcanic origin, tropical areas etc. Examples of such organisms, for instance, include prokaryotic microorganisms, such as eubacteria and archaebacteria (Bronneomerier, K. and Staudenbauer, W. L., D. R. Woods (ed), the Clostridia and Biotechnology, Butterworth Publishers, Stoneham, M. A. (1993), among other organisms.

Thermostable enzymes exhibit greater storage life capacity and organic solvent resistance, as compared to their mesophilic counterparts.

There are applications in industry and in research for thermostable enzymes which exhibit enzyme activity at a desired minimum temperature. An example of this occurs in molecular diagnostics wherein reporter molecules must survive long term storage at room temperature or higher or they need to function in unusual environments, and the assays which employ them are performed at room temperature where the activity of thermostable enzymes is generally very low.

FIG. 1 illustrates the full length DNA sequence (SEQ ID NO:1) and corresponding deduced amino acid sequence (SEQ ID NO:2) Thermococcus 9N2 Beta-glycosidase.

Applicant has found that it is possible to provide thermostable enzymes which have improved activity at lower temperatures.

More particularly, Applicant has found that the activity of thermophilic enzymes can be improved at lower temperatures while maintaining the temperature stability of such enzymes.

Still more particularly, Applicant has found there can be obtained a thermostable enzyme with improved activity at lower temperature by subjecting to mutagenesis a thermostable enzyme or polynucleotide encoding such thermostable enzyme followed by a screening of the resulting mutants to identify a mutated enzyme or a mutated polynucleotide encoding a mutated enzyme, which mutated enzyme retains thermostability and which has an enzyme activity at lower temperatures which is at least two (2) times greater than a corresponding non-mutated enzyme.

The thermostable enzymes and mutated thermostable enzymes are stable at temperatures up to 60° C. and preferably are stable at temperatures of up to 70° C. and more preferably at temperatures up to 95° C. and higher.

Increased activity of mutated thermostable enzymes at lower temperatures is meant to encompass activities which are at least two-fold, preferably at least four-fold, and more preferably at least ten-fold greater than that of the corresponding wild-type enzyme.

Increased enzyme activity at lower temperatures means that enzyme activity is increased at a temperature below 50° C., preferably below 40° C. and more preferably below 10° C. Thus, in comparing enzyme activity at a lower temperature between the mutated and non-mutated enzyme, the enzyme activity of the mutated enzyme at defined lower temperatures is at least 2 times greater than the enzyme activity of the corresponding non-mutated enzyme.

Thus, lower temperatures and lower temperature ranges include temperatures which are at least 5° C. less than the temperature at which thermostable enzymes are stable, which includes temperatures below 55° C., 50° C., 45° C., 40° C., 35° C., 30° C., 25° C. and 20° C. with below 50° C., being preferred, and below 40° C. being more preferred, and below 30° C. (or approximately room temperature) being most preferred.

In accordance with an aspect of the present invention, the lower temperature or lower temperature range at which a greater enzyme activity is desired is determined and a thermostable enzyme(s), or polynucleotide encoding such enzyme(s), are subjected to mutagenesis and the resulting mutants are screened to determine mutated enzymes (or polynucleotide encoding mutated enzymes) which retain thermostability and which have a minimum desired increase in enzyme activity at the desired temperature or temperature range.

Thermostable enzymes are enzymes which have activity, i.e. are not degraded, at temperatures above 60° C. Thermostable enzymes also have increased storage life, and high resistance to organic solvents.

Thermostable enzymes may be isolated from thermophilic organisms such as those which are found in elevated temperatures such as in hot springs, volcanic areas and tropical areas. Examples of thermophilic organisms are prokaryotic organisms for example, thermophilic bacteria such as eubacteria and archaebacteria.

The DNA from these thermostable organisms can then be isolated by available techniques that are described in the literature. The IsoQuick® nucleic acid extraction kit (MicroProbe Corporation) is suitable for this purpose.

The term "derived" or "isolated" means that material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated.

The DNA isolated or derived from these microorganisms can preferably be inserted into a vector. Such vectors are preferably those containing expression regulatory sequences, including promoters, enhancers and the like. Such polynucleotides can be part of a vector and/or a composition and still be isolated, in that such vector or composition is not part of its natural environment.

Alternatively, enzymes not known to have thermostable properties can be screened for such properties by inserting the DNA encoding the enzyme in an expression vector and transforming a suitable host as hereinafter described, such that the enzyme may be expressed and screened for positive thermostable activity.

As representative examples of expression vectors which may be used there may be mentioned viral particles, baculovirus, phage, plasmids, phagemids, cosmids, phosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, aspergillus, yeast, etc.) Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE70, pQE60, pQE-9Qiagen), psiX174, pBluescript SK, pBluescript KS, (Stratagene); pTRC99a, pKK223-3, pKK233-3, pDR540, pRIT2T (Pharmacia); Eukaryotic: pWLNEO, pXT1, pSG (Stratagene) pSVK3, pBPV, PMSG, pSVLSV40(Pharmacia). Any other plasmid or vector may be used as long as they are replicable and viable in the host.

The DNA derived from a microorganism(s) may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence (s) (promoter) to direct mRNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloramphenicol transferase) vectors or other vectors with selectable markers.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operon encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the peroplasmic space or extracellular medium.

The DNA selected and isolated as hereinabove described is introduced into a suitable host to prepare a library which is screened for the desired enzyme activity. The selected DNA is preferably already in a vector which includes appropriate control sequences whereby selected DNA which encodes for an enzyme may be expressed, for detection of the desired activity. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by transformation, calcium phosphate transfection, DEAE-Dextran mediated transfection, or electroporation (Davis, L., Dibner, M., Battey, I., Basic Methods in Molecular Biology, (1986)).

As representative examples of appropriate hosts, there may be mentioned: bacterial cells, such as *E. coli*, Streptomyces, *Salmonella typhimurium*; fungal cells, such as yeast; insect cells such as Drosophila S2and Spodoptera Sf9; animal cells such as CHO, COS or Bowes melanoma; adenoviruses; plant cells, etc. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa 293 and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells are genetically engineered (transduced or transformed or transfected) with the vectors. The engineered host cells can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

The isolated DNA encoding a thermostable enzyme is subjected to mutagenesis techniques, with the preferred type of mutagenesis techniques being set forth below.

The term "error-prone PCR" refers to a process for performing PCR under conditions where the copying fidelity of the DNA polymerase is low, such that a high rate of point mutations is obtained along the entire length of the PCR product. Leung, D. W., et al., Technique, 1:11–15 (1989) and Caldwell, R. C. & Joyce G. F., PCR Methods Applic., 2:28–33 (1922).

The term "oligonucleotide directed mutagenesis" refers to a process which allows for the generation of site-specific mutations in any cloned DNA segment of interest. Reidhaar-Olson, J. F. & Sauer, R. T., et al., Science, 241:53–57 (1988).

The term "assembly PCR" refers to a process which involves the assembly of a PCR product from a mixture of small DNA fragments. A large number of different PCR reactions occur in parallel in the same vial, with the products of one reaction priming the products of another reaction.

The term "sexual PCR mutagenesis" refers to forced homologous recombination between DNA molecules of different but highly related DNA sequence in vitro, caused by random fragmentation of the DNA molecule based on sequence homology, followed by fixation of the crossover by primer extension in a PCR reaction. Stemmer, W. P., PNAS, USA, 91:10747–10751 (1994)

The term "in vivo mutagenesis" refers to a process of generating random mutations in any cloned DNA of interest which involves the propagation of the DNA in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA.

The term "cassette mutagenesis" refers to any process for replacing a small region of a double stranded DNA molecule with a synthetic oligonucleotide "cassette" that differs from the native sequence. The oligonucleotide often contains completely and/or partially randomized native sequence.

The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis. Arkin, A. P. and Youvan, D. C., PNAS, U.S.A., 89:7811–7815 (1992).

The term "exponential ensemble mutagenesis" refers to a process for generating combinatorial libraries with a high percentage of unique and functional mutants, wherein small groups of residues are randomized in parallel to identify, at each altered position, amino acids which lead to functional proteins, Delegrave, S. and Youvan, D. C Biotechnology Research, 11:1548–1552 (1993); and random and site-directed mutagenesis, Arnold, F. H., Current Opinion in Biotechnology, 4:450–455 (1993). All of the references mentioned above are hereby incorporated by reference in their entirety.

As can be seen from the above mutagenesis techniques, the DNA encoding an enzyme having the desired activity may be subject to mutagenesis alone, i.e. as naked DNA, or the DNA may be subjected to mutagenesis after insertion into an appropriate vector as hereinabove described. These techniques are referred to as in vitro mutagenesis.

Alternatively, in vivo mutagenesis may be performed wherein the DNA is subjected to mutagenesis while it is within a cell or living organism. A preferred example of this technique utilizes the XL1 Red Strain of E. coli (Stratagene, Inc.) which has its DNA repair genes, MutH, MutL and MutS, deleted such that many different mutations occur in a short time. Up to 10,000 mutations may take place within a 30 hour time span such that an entire mutated DNA library may be prepared from mutated DNA by procedures known in the art.

After an appropriate amount of time to allow mutations to take place, the mutated DNA is excised from the host cell in the case of in vivo mutagenesis and inserted in another appropriate vector and used to transform a non-mutator host, for example, XL1 Blue strain of E. coli after which a mutated DNA library is prepared. In the case of in vitro mutagenesis, if the mutated DNA has previously been inserted in an appropriate expression vector, said vector is then used directly to transform an appropriate non-mutator host for the preparation of a mutated DNA library, if the mutagenized DNA is not in an appropriate expression vector.

A library is prepared for screening by transforming a suitable organism. Hosts, particularly those specifically identified herein as preferred, are transformed by artificial introduction of the vectors containing the mutated DNA by inoculation under conditions conducive for such transformation.

The resultant libraries of transformed clones are then screened for clones which display activity for the enzyme of interest in a phenotypic assay for enzyme activity.

For example, having prepared a multiplicity of clones from DNA mutagenized by one of the techniques described above, such clones are screened for the specific enzyme activity of interest.

For example, the clones containing the mutated DNA are now subject to screening procedures to determine their activity within both higher temperatures and within the desired lower temperature range to identify mutants which have the desired increase in activity within the lower temperature range when compared to the corresponding wild-type thermostable enzyme which is non-mutated.

Positively identified clones, i.e. those which contain mutated DNA sequences which express thermostable enzymes which are thermostable and yet have an increased activity at least two times than the corresponding wild-type enzyme at temperatures within the lower temperature range, are isolated and sequenced to identify the DNA sequence. As an example, phosphatase activity at the desired lower temperature ranges may be identified by exposing the clones, and thus the thermostable enzyme and testing its ability to cleave an appropriate substrate.

In Example 1 phosphatase and β-galactosidase activity are measured by comparing the wild-type enzymes to the enzymes subjected to mutagenesis. As can be seen from the results of Example 1, mutagenesis of a wild-type phosphatase and β-galactosidase thermophilic enzyme produce mutated enzymes which were 3 and 2.5 times more active, respectively, at lower temperatures than the corresponding wild-type enzymes within the lower temperature range of room temperature.

In the case of protein engineering, after subjecting a thermophilic enzyme to mutagenesis, the mutagenized enzyme is screened for the desired activity namely, increased activity at lower temperatures while maintaining activity at the higher temperatures. Any of the known techniques for protein mutagenesis may be employed, with particularly preferred mutagenesis techniques being those discussed above.

As a representative list of enzymes which may be mutagenized in accordance with the aspects of the present invention, there may be mentioned, the following enzymes and their functions:

1 Lipase/Esterase
  a. Enantioselective hydrolysis of esters (lipids)/thioesters
    1) Resolution of racemic mixtures
    2) Synthesis of optically active acids or alcohols from meso-diesters
  b. Selective syntheses
    1) Regiospecific hydrolysis of carbohydrate esters
    2) Selective hydrolysis of cyclic secondary alcohols
  a. Synthesis of optically active esters, lactones, acids, alcohols
    1) Transesterification of activated/nonactivated esters
    2) Interesterification
    3) Optically active lactones from hydroxyesters
    4) Regio- and enantioselective ring opening of anhydrides
  d. Detergents
  e. Fat/Oil conversion
  f. Cheese ripening 2 Protease
  a. Ester/amide synthesis
  b. Peptide synthesis
  c. Resolution of racemic mixtures of amino acid esters
  d. Synthesis of non-natural amino acids
  e. Detergents/protein hydrolysis 3 Glycosidase/Glycosyl transferase
  a. Sugar/polymer synthesis
  b. Cleavage of glycosidic linkages to form mono, di- and oligosaccharides
  c. Synthesis of complex oligosaccharides
  d. Glycoside synthesis using UDP-galactosyl transferase
  e. Transglycosylation of disaccharides, glycosyl fluorides, aryl galactosides
  f. Glycosyl transfer in oligosaccharide synthesis
  g. Diastereoselective cleavage of β-glucosylsulfoxides
  h. Asymmetric glycosylations i. Food processing
j. Paper processing
4 Phosphatase/Kinase
  a. Synthesis/hydrolysis of phosphate esters
    1) Regio-, enantioselective phosphorylation
    2) Introduction of phosphate esters
    3) Synthesize phospholipid precursors
    4) Controlled polynucleotide synthesis
  b. Activate biological molecule
  c. Selective phosphate bond formation without protecting groups
5 Mono/Dioxygenase
  a. Direct oxyfunctionalization of unactivated organic substrates
  b. Hydroxylation of alkane, aromatics, steroids
  c. Epoxidation of alkenes
  d. Enantioselective sulphoxidation
  e. Regio- and stereoselective Bayer-Villiger oxidations
6 Haloperoxidase
  a. Oxidative addition of halide ion to nucleophilic sites
  b. Addition of hypohalous acids to olefinic bonds
  c. Ring cleavage of cyclopropanes
  d. Activated aromatic substrates converted to ortho and para derivatives
  e. 1.3 diketones converted to 2-halo-derivatives
  f. Heteroatom oxidation of sulfur and nitrogen containing substrates
  g. Oxidation of enol acetates, alkynes and activated aromatic rings
7 Lignin peroxidase/Diarylpropane peroxidase
  a. Oxidative cleavage of C—C bonds
  b. Oxidation of benzylic alcohols to aldehydes
  c. Hydroxylation of benzylic carbons
  d. Phenol dimerization
  e. Hydroxylation of double bonds to form diols
  f. Cleavage of lignin aldehydes
8 Epoxide hydrolase
  a. Synthesis of enantiomerically pure bioactive compounds
  b. Regio- and enantioselective hydrolysis of epoxide
  c. Aromatic and olefinic epoxidation by monooxygenases to form epoxides
  d. Resolution of racemic epoxides
  e. Hydrolysis of steroid epoxides
9 Nitrile hydratase/nitrilase
  a. Hydrolysis of aliphatic nitriles to carboxamides
  b. Hydrolysis of aromatic, heterocyclic, unsaturated aliphatic nitriles to corresponding acids
  c. Hydrolysis of acrylonitrile
  d. Production of aromatic and carboxamides, carboxylic acids (nicotinamide, picolinamide, isonicotinamide)
  e. Regioselective hydrolysis of acrylic dinitrile
  f. α-amino acids from α-hydroxynitriles
10 Transaminase
  a. Transfer of amino groups into oxo-acids
11 Amidase/Acylase
  a. Hydrolysis of amides, amidines, and other C—N bonds
  b. Non-natural amino acid resolution and synthesis The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

EXAMPLE 1

Mutagenesis of Positive Enzyme Activity Clones

Mutagenesis was performed on two different enzymes (alkaline phosphatase and β-glycosidase), using the two different strategies described here, to generate new enzymes which exhibit a higher degree of activity at lower temperatures than the wild-type enzymes.

Alkaline Phosphatase

The XL1-Red strain (Stratagene) was transformed with DNA encoding an alkaline phosphatase (in plasmid pBluescript) from the organism OC9a according to the manufacturer's protocol. A 5 ml culture of LB+0.1 mg/ml ampicillin was inoculated with 200 µl of the transformation. The culture was allowed to grow at 37° C. for 30 hours. A miniprep was then performed on the culture, and screening was performed by transforming 2 µl of the resulting DNA into XL-1 Blue cells (Stratagene) according to the manufacturer's protocol.

Standard Alkaline Phosphatase Screening Assay
  →Plate on LB/amp plates→Lift colonies with Duralon UV (Stratagene) or HATF (Millipore) membranes→Lyse in chloroform vapors for 30 seconds→Heat kill for 30 minutes at 85° C.→Develop filter at room temperature in BCIP buffer→Watch as filter develops and identify and pick fastest developing colonies ("positives")→Restreak "positives" onto a BCIP plate.

BCIP Buffer
  20 mm CAPS pH 9.0
  1 mm $MgCl_2$
  0.01 mm $ZnCl_2$
  0.1 mg/ml BCIP The mutated OC9a phosphatase took 10 minutes to develop color and the wild type enzyme took 30 minutes to develop color in the screening assay.

Beta-Glycosidase

This protocol was used to mutagenize DNA encoding Thermococcus 9N2 Beta-Glycosidase. This DNA sequence is set forth in FIG. 1.

PCR
  2 microliters dNTP's (10 mM Stocks)
  10 microliters 10×PCR Buffer
  0.5 microliters pBluescript vector containing Beta-glycosidase DNA (100 nanograms)
  20 microliters 3' Primer (100 pmol)
  20 microliters 5' Primer (100 pmol)
  16 microliters $MnCl\ 4H_2O$ (1.25 mM Stock)
  24.5 microliters $H_2O$
  1 microliter Taq Polymerase (5.0 Units)
  100 microliters total Reaction Cycle
  95° C. 15 seconds
  58° C. 30 seconds
  72° C. 90 seconds
  25 cycles (10 minute extension at 72° C.–4° C. incubation)
  Run 5 microliters on a 1% agarose gel to check the reaction.
  Purify on a Qiaquick column (Qiagen).
  Resuspend in 50 microliters $H_2O$.

Restriction Digest
  25 microliters purified PCR product
  10 microliters NEB Buffer #2
  3 microliters Kpn I (10 U/microliter)
  3 microliters EcoR1 (20 U/microliter)

59 microliters H₂O
Cut for 2 hours at 37° C.
Purify on a Qiaquick column (Qiagen).
Elute with 35 microliters H₂O.
Ligation
10 microliters Digested PCR product
5 microliters pBluescript Vector (cut with EcoRI/KpnI and phosphatased with shrimp alkaline phosphatase)
4 microliters 5× Ligation Buffer
1 microliter T4 DNA Ligase (BRL)
Ligate overnight.
Transform into M15pREP4 cells using electroporation.
Plate 100 or 200 microliters onto LB amp meth kan plates, grow overnight at 37 degrees celsius.

Beta-Glycosidase Assay

Perform glycosidase assay to screen for mutants as follows. The filter assay uses buffer Z (see recipe below) containing 1 mg/ml of the substrate 5-bromo-4-chloro-3-indolyl-β-o-glucopyranoside (XGLU) (Diagnostic Chemicals Limited or Sigma).

Z-Buffer: (referenced in Miller, J. H. (1992) A Short Course in Bacterial Genetics, p. 445.)

per liter:
  Na₂HPO₄-7H₂O 16.1 g
  NaH₂PO₄-H₂O 5.5 g
  KCl 0.75 g
  MgSO₄-7₂O 0.246 g
  β-mercaptoethanol 2.7 ml (1) Adjust pH to 7.0

Perform colony lifts using Millipore HATF membrane filters.

(2) Lyse colonies with chloroform vapor in 150 mm glass petri dishes.

(3) Transfer filters to 100 mm glass petri dishes containing a piece of Whatman 3 MM filter paper saturated with Z buffer containing 1 mg/ml XGLU. After transferring filter bearing lysed colonies to the glass petri dish, maintain dish at room temperature.

(4) "Positives" were observed as blue spots on the filter membranes ("positives" are spots which appear early). Use the following filter rescue technique to retrieve plasmid from lysed positive colony. Use pasteur pipette (or glass capillary tube) to core blue spots on the filter membrane. Place the small filter disk in an Epp tube containing 20 μl water. Incubate the Epp tube at 75° C. for 5 minutes followed by vortexing to elute plasmid DNA off filter. Transform this DNA into electrocompetent E. coli cells. Repeat filter-lift assay on transformation plates to identify "positives." Return transformation plates to 37° C. incubator after filter lift to regenerate colonies. Inoculate 3 ml LBamp liquid with repurified positives and incubate at 37° C. overnight. Isolate plasmid DNA from these cultures and sequence plasmid insert.

The β-glycosidase subjected to mutagenesis acted on XGLU 2.5 times more efficiently than wild-type β-glycosidase.

---

What is claimed is:

1. A method for providing a thermostable enzyme having improved enzyme activities as compared to a corresponding wild-type enzyme at lower temperatures, comprising:
    (a) subjecting at least one polynucleotide encoding an enzyme which is stable at a temperature of at least 60° C. to a random mutagenesis; and
    (b) screening mutant enzymes produced in (a) for a mutated enzyme or for a polynucleotide encoding a mutated enzyme, wherein the mutated enzyme is stable at a temperature of at least 60° C.; has an enzyme activity at a temperature at least 10° C. below its optimal temperature range; and has activity greater than the enzyme encoded by the polynucleotide of step (a) prior to mutagenesis.

2. The method of claim 1, wherein the enzyme is selected from the group consisting of lipase, esterase, protease, glycosidase, glycosyl transferase, phosphatase, kinase, monoxygenase, dioxygenase, haloperoxidase, lignin peroxidase, diarylpropane peroxidase, epoxide hydrolase, nitrite hydratase, nitrile nitrilase, transaminase, amidase and acylase.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
       ( A ) LENGTH: 4463 base pairs
       ( B ) TYPE: nucleic acid
       ( C ) STRANDEDNESS: single
       ( D ) TOPOLOGY: linear ( i i ) MOLECULE TYPE: Genomic DNA ( i x ) FEATURE:
       ( A ) NAME/KEY: Coding Sequence
       ( B ) LOCATION: 1...4461

( x i ) SEQUENCE DESCRIPTION: SEQ ID NO:1:

```
AAT  TCC  AGG  ATG  AAC  CTC  ATC  TGG  TCG  GTC  TTG  AGC  TTG  TAC  ATT  CCG        48
Asn  Ser  Arg  Met  Asn  Leu  Ile  Trp  Ser  Val  Leu  Ser  Leu  Tyr  Ile  Pro
 1              5                        10                       15

GAA  CCG  ATG  GGG  TTC  TCG  CTG  TTG  GCG  TAC  TTT  ATC  GGG  TCT  TTG  ATG        96
Glu  Pro  Met  Gly  Phe  Ser  Leu  Leu  Ala  Tyr  Phe  Ile  Gly  Ser  Leu  Met
                  20                       25                       30

TCC  TTC  CAG  ATG  TGC  TCA  GGG  ACG  ATC  GGG  ATC  TGG  AGC  CAG  TCC  CAC       144
Ser  Phe  Gln  Met  Cys  Ser  Gly  Thr  Ile  Gly  Ile  Trp  Ser  Gln  Ser  His
             35                       40                       45

TCC  GCG  TGC  GGA  TCG  CTG  AAG  ATG  AAA  TCA  ACG  GTT  CTG  TCG  TCA  ACG       192
Ser  Ala  Cys  Gly  Ser  Leu  Lys  Met  Lys  Ser  Thr  Val  Leu  Ser  Ser  Thr
        50                       55                       60

ACC  TTG  ACC  TCC  TTG  AGC  CAG  CCC  CAA  ACG  CTC  GAG  AAG  GAG  GCA  CCG       240
Thr  Leu  Thr  Ser  Leu  Ser  Gln  Pro  Gln  Thr  Leu  Glu  Lys  Glu  Ala  Pro
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 65  |     |     |     |     | 70  |     |     |     |     | 75  |     |     |     |     | 80  |      |
| GTG | TGG | TTC | TTC | GCG | AGG | AAG | GTG | AAC | TTA | ACG | TCT | TCA | GCG | GTT | AGG | 288  |
| Val | Trp | Phe | Phe | Ala | Arg | Lys | Val | Asn | Leu | Thr | Ser | Ser | Ala | Val | Arg |      |
|     |     |     |     | 85  |     |     |     |     | 90  |     |     |     |     | 95  |     |      |
| GGC | TTT | CCG | TCC | TGC | CAG | GTT | AGG | CCC | TCC | TTC | AGC | TTG | ACC | TCG | GTG | 336  |
| Gly | Phe | Pro | Ser | Cys | Gln | Val | Arg | Pro | Ser | Phe | Ser | Leu | Thr | Ser | Val |      |
|     |     |     |     | 100 |     |     |     |     | 105 |     |     |     |     | 110 |     |      |
| TTG | TCG | TTG | ATC | CAC | TTC | CCA | GAC | TCG | GCC | AGC | CAG | GGA | ATG | AGC | TGG | 384  |
| Leu | Ser | Leu | Ile | His | Phe | Pro | Asp | Ser | Ala | Ser | Gln | Gly | Met | Ser | Trp |      |
|     |     |     | 115 |     |     |     |     | 120 |     |     |     |     | 125 |     |     |      |
| TCC | TTC | AGC | GGG | TCG | AAG | AAC | AGG | GGC | TCG | ATG | AGG | CTA | TCG | TGC | CTG | 432  |
| Ser | Phe | Ser | Gly | Ser | Lys | Asn | Arg | Gly | Ser | Met | Arg | Leu | Ser | Cys | Leu |      |
|     |     | 130 |     |     |     |     | 135 |     |     |     |     | 140 |     |     |     |      |
| CTG | CGG | CCC | AGG | AGA | CAA | GGG | GAT | AGT | TCG | TCG | GCT | GAC | TCC | ACA | GAC | 480  |
| Leu | Arg | Pro | Arg | Arg | Gln | Gly | Asp | Ser | Ser | Ser | Ala | Asp | Ser | Thr | Asp |      |
| 145 |     |     |     |     | 150 |     |     |     |     | 155 |     |     |     |     | 160 |      |
| CGC | CTC | CAA | CGT | AGA | GGG | TTT | CAT | TCC | TGG | GAA | GCT | CCT | CGG | CGC | GGA | 528  |
| Arg | Leu | Gln | Arg | Arg | Gly | Phe | His | Ser | Trp | Glu | Ala | Pro | Arg | Arg | Gly |      |
|     |     |     |     | 165 |     |     |     |     | 170 |     |     |     |     | 175 |     |      |
| CGT | AGC | CCG | CGA | ATC | CAA | CAA | GGC | TTG | AAA | CCA | TCA | GCA | CTG | CCA | GCA | 576  |
| Arg | Ser | Pro | Arg | Ile | Gln | Gln | Gly | Leu | Lys | Pro | Ser | Ala | Leu | Pro | Ala |      |
|     |     |     | 180 |     |     |     |     | 185 |     |     |     |     | 190 |     |     |      |
| GCA | AAC | CAA | GGA | TTC | GTC | TCA | TGC | GCA | CCA | CCC | CAG | ACC | GCG | AGG | GTC | 624  |
| Ala | Asn | Gln | Gly | Phe | Val | Ser | Cys | Ala | Pro | Pro | Gln | Thr | Ala | Arg | Val |      |
|     |     | 195 |     |     |     |     | 200 |     |     |     |     | 205 |     |     |     |      |
| TGT | AGT | TAT | AAA | AAC | GCG | CTC | CAA | ATT | TAT | AAA | ACT | TTG | GGT | TCT | GTT | 672  |
| Cys | Ser | Tyr | Lys | Asn | Ala | Leu | Gln | Ile | Tyr | Lys | Thr | Leu | Gly | Ser | Val |      |
|     | 210 |     |     |     |     | 215 |     |     |     |     | 220 |     |     |     |     |      |
| ATA | AAA | TTG | GGG | CAA | AAA | TTA | AAA | TCG | GCA | AAC | CTT | ATA | AGG | GAG | AAA | 720  |
| Ile | Lys | Leu | Gly | Gln | Lys | Leu | Lys | Ser | Ala | Asn | Leu | Ile | Arg | Glu | Lys |      |
| 225 |     |     |     |     | 230 |     |     |     |     | 235 |     |     |     |     | 240 |      |
| GGC | AAA | GTT | ACA | TGG | GGG | TTG | GTC | TAT | GCT | ACC | AGA | AGG | CTT | TCT | CTG | 768  |
| Gly | Lys | Val | Thr | Trp | Gly | Leu | Val | Tyr | Ala | Thr | Arg | Arg | Leu | Ser | Leu |      |
|     |     |     |     | 245 |     |     |     |     | 250 |     |     |     |     | 255 |     |      |
| GGG | CGT | GTC | CCA | GTC | CGG | CTT | TCA | GTT | CGA | GAT | GGG | CGA | CAA | GCT | CAG | 816  |
| Gly | Arg | Val | Pro | Val | Arg | Leu | Ser | Val | Arg | Asp | Gly | Arg | Gln | Ala | Gln |      |
|     |     |     | 260 |     |     |     |     | 265 |     |     |     |     | 270 |     |     |      |
| GAG | GAA | CAT | TCC | GAA | CAC | AGA | CTG | GTG | GAA | GTG | GGT | CAG | GGA | TCC | CTT | 864  |
| Glu | Glu | His | Ser | Glu | His | Arg | Leu | Val | Glu | Val | Gly | Gln | Gly | Ser | Leu |      |
|     |     | 275 |     |     |     |     | 280 |     |     |     |     | 285 |     |     |     |      |
| CAA | CAT | AAA | GAG | GGA | ACT | CGT | CAG | CGG | CGA | CCT | GCC | CGA | GGA | GGG | GAT | 912  |
| Gln | His | Lys | Glu | Gly | Thr | Arg | Gln | Arg | Arg | Pro | Ala | Arg | Gly | Gly | Asp |      |
|     | 290 |     |     |     |     | 295 |     |     |     |     | 300 |     |     |     |     |      |
| AAA | CAA | CTA | CGA | ACT | TTA | CGA | GAA | GGA | TCA | CCG | CCT | CGC | CAG | AGA | CCT | 960  |
| Lys | Gln | Leu | Arg | Thr | Leu | Arg | Glu | Gly | Ser | Pro | Pro | Arg | Gln | Arg | Pro |      |
| 305 |     |     |     |     | 310 |     |     |     |     | 315 |     |     |     |     | 320 |      |
| CGG | TCT | GAA | CGT | TTA | CAG | GAT | TGG | AAT | AGA | GTG | GAG | CAG | GAT | CTT | TCC | 1008 |
| Arg | Ser | Glu | Arg | Leu | Gln | Asp | Trp | Asn | Arg | Val | Glu | Gln | Asp | Leu | Ser |      |
|     |     |     |     | 325 |     |     |     |     | 330 |     |     |     |     | 335 |     |      |
| CTG | GCC | AAC | GTG | GTT | TGT | GGA | GGT | CGT | GCG | GGA | CAG | CTA | CGG | ACT | CGT | 1056 |
| Leu | Ala | Asn | Val | Val | Cys | Gly | Gly | Arg | Ala | Gly | Gln | Leu | Arg | Thr | Arg |      |
|     |     |     | 340 |     |     |     |     | 345 |     |     |     |     | 350 |     |     |      |
| GAA | GGA | CGT | CAA | AAT | CGA | AGA | CAC | GCT | CGA | AGA | GCT | CGA | CGA | GAT | AGC | 1104 |
| Glu | Gly | Arg | Gln | Asn | Arg | Arg | His | Ala | Arg | Arg | Ala | Arg | Arg | Asp | Ser |      |
|     |     | 355 |     |     |     |     | 360 |     |     |     |     | 365 |     |     |     |      |
| GAA | TCA | TCA | GGA | GAT | AGC | CTA | CTA | CCG | CCG | CGT | TAT | AGA | GCA | CCT | CAG | 1152 |
| Glu | Ser | Ser | Gly | Asp | Ser | Leu | Leu | Pro | Pro | Arg | Tyr | Arg | Ala | Pro | Gln |      |
|     |     | 370 |     |     |     |     | 375 |     |     |     |     | 380 |     |     |     |      |
| GGA | GCT | GGG | CTT | CAA | GGT | CAT | CGT | GAA | CCT | CAA | CCA | CTT | CAC | GCT | CCC | 1200 |
| Gly | Ala | Gly | Leu | Gln | Gly | His | Arg | Glu | Pro | Gln | Pro | Leu | His | Ala | Pro |      |

```
                    385                           390                           395                           400

CCT  CTG  GCT  TCA  CGA  TCC  GAT  AAT  CGC  GAG  GGA  GAA  GGC  CCT  CAC  CAA            1248
Pro  Leu  Ala  Ser  Arg  Ser  Asp  Asn  Arg  Glu  Gly  Glu  Gly  Pro  His  Gln
                    405                      410                           415

CGG  GAT  TGG  CTG  GGT  CGG  GCA  GGA  GAG  CGT  GGT  GGA  GTT  CGC  CAA  GTA            1296
Arg  Asp  Trp  Leu  Gly  Arg  Ala  Gly  Glu  Arg  Gly  Gly  Val  Arg  Gln  Val
               420                           425                      430

CGC  GGC  GTA  CAT  CGC  GAA  CGC  ACT  CGG  GGA  CCT  CGT  TAT  GTG  GAG  CAC            1344
Arg  Gly  Val  His  Arg  Glu  Arg  Thr  Arg  Gly  Pro  Arg  Tyr  Val  Glu  His
          435                           440                      445

CTT  CAA  CGA  GCC  GAT  GGT  CGT  TGT  GGA  GCT  CGG  TTA  CCT  CGC  GCC  CTA            1392
Leu  Gln  Arg  Ala  Asp  Gly  Arg  Cys  Gly  Ala  Arg  Leu  Pro  Arg  Ala  Leu
     450                           455                      460

CTC  CGG  CTT  TCC  GCC  GGG  GGT  TAT  GAA  CCC  CGA  GGC  GGC  AAA  GCT  GGC            1440
Leu  Arg  Leu  Ser  Ala  Gly  Gly  Tyr  Glu  Pro  Arg  Gly  Gly  Lys  Ala  Gly
465                      470                           475                      480

AAT  CCT  CAA  CAT  GAT  AAA  CGC  CCA  CGC  ACT  GGC  CTA  CAA  GAT  GAT  AAA            1488
Asn  Pro  Gln  His  Asp  Lys  Arg  Pro  Arg  Thr  Gly  Leu  Gln  Asp  Asp  Lys
                    485                      490                           495

GAA  GTT  CGA  CAG  GGT  AAA  GGC  CGA  GGA  TTC  CCG  CTC  CGA  GGC  CGA  GGT            1536
Glu  Val  Arg  Gln  Gly  Lys  Gly  Arg  Gly  Phe  Pro  Leu  Arg  Gly  Arg  Gly
               500                           505                      510

CGG  GAT  AAT  CTA  CAA  CAA  CAT  AGG  CGT  TGC  CTA  TCC  ATA  CGA  CTC  CAA            1584
Arg  Asp  Asn  Leu  Gln  Gln  His  Arg  Arg  Cys  Leu  Ser  Ile  Arg  Leu  Gln
          515                           520                      525

CGA  CCC  AAA  GGA  CGT  GAA  AGC  TGC  AGA  AAA  CGA  CAA  CTA  CTT  CCA  CAG            1632
Arg  Pro  Lys  Gly  Arg  Glu  Ser  Cys  Arg  Lys  Arg  Gln  Leu  Leu  Pro  Gln
     530                           535                      540

CGG  GCT  CTT  CTT  CGA  CGC  AAT  CCA  CAA  GGG  CAA  GCT  CAA  CAT  CGA  GTT            1680
Arg  Ala  Leu  Leu  Arg  Arg  Asn  Pro  Gln  Gly  Gln  Ala  Gln  His  Arg  Val
545                      550                           555                      560

CGA  CGG  GAC  CTT  CGT  CAA  AGT  TCG  GCA  TCT  CAG  GGG  GAA  CGA  CTG  GAT            1728
Arg  Arg  Asp  Leu  Arg  Gln  Ser  Ser  Ala  Ser  Gln  Gly  Glu  Arg  Leu  Asp
                    565                      570                           575

AGG  CGT  CTA  CTA  CAC  GAG  AGA  AGT  CGT  CAG  GTA  TTC  GGA  GCC  CAA  GTT            1776
Arg  Arg  Leu  Leu  His  Glu  Arg  Ser  Arg  Gln  Val  Phe  Gly  Ala  Gln  Val
               580                           585                      590

CCC  GAG  CAT  ACC  CCT  GAT  ATC  CTT  CCG  GGG  AGT  TCA  CAA  CTA  CGG  CTA            1824
Pro  Glu  His  Thr  Pro  Asp  Ile  Leu  Pro  Gly  Ser  Ser  Gln  Leu  Arg  Leu
          595                           600                      605

CGC  CTG  CAG  GCC  CGG  GAG  TTC  TTC  CGC  CGA  CGG  AAG  GCC  CGT  AAG  CGA            1872
Arg  Leu  Gln  Ala  Arg  Glu  Phe  Phe  Arg  Arg  Arg  Lys  Ala  Arg  Lys  Arg
     610                           615                      620

CAT  CGG  CTG  GGA  GAT  CTA  TCC  GGA  GGG  GAT  CTA  CGA  CTC  GAT  AAG  AGA            1920
His  Arg  Leu  Gly  Asp  Leu  Ser  Gly  Gly  Asp  Leu  Arg  Leu  Asp  Lys  Arg
625                      630                           635                      640

GGC  CAA  CAA  ATA  CGG  GGT  CCC  GGT  TTA  CGT  CAC  CGA  AAA  CGG  AAT  AGC            1968
Gly  Gln  Gln  Ile  Arg  Gly  Pro  Gly  Leu  Arg  His  Arg  Lys  Arg  Asn  Ser
                    645                      650                           655

CGA  TTC  AAC  CAC  CCT  GCG  GCC  GTA  CTA  CCT  CGC  GAG  CCA  TGT  AGC  GAA            2016
Arg  Phe  Asn  His  Pro  Ala  Ala  Val  Leu  Pro  Arg  Glu  Pro  Cys  Ser  Glu
               660                           665                      670

GAT  GGA  GGC  GTA  CGA  GGC  GGG  TTA  CGA  CGT  CAG  GGG  CTA  CCT  CTA  CTG            2064
Asp  Gly  Gly  Val  Arg  Gly  Gly  Leu  Arg  Arg  Gln  Gly  Leu  Pro  Leu  Leu
          675                           680                      685

GGC  GCT  GAC  CGA  CAA  CTA  CGA  GTG  GGC  CCT  CGG  TTT  CAG  GAT  GAG  GTT            2112
Gly  Ala  Asp  Arg  Gln  Leu  Arg  Val  Gly  Pro  Arg  Phe  Gln  Asp  Glu  Val
     690                           695                      700

CGG  CCT  CTA  AGT  GGA  TCT  CAT  AAC  CAA  GGA  GAG  AAC  ACC  GCG  GGA  GGA            2160
Arg  Pro  Leu  Ser  Gly  Ser  His  Asn  Gln  Gly  Glu  Asn  Thr  Ala  Gly  Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 705 |     |     |     |     | 710 |     |     |     |     | 715 |     |     |     |     | 720 |      |
| AAG | CGT | AAA | GGT | TTA | GGG | CAT | CGT | GGA | GAA | CAA | CGG | AGT | GAG | CAA | GGA | 2208 |
| Lys | Arg | Lys | Gly | Leu | Gly | His | Arg | Gly | Glu | Gln | Arg | Ser | Glu | Gln | Gly |      |
|     |     |     |     | 725 |     |     |     |     | 730 |     |     |     |     | 735 |     |      |
| AAT | CCG | GGA | GAA | GTT | CGG | ACT | TGG | GTG | AAG | GTA | ATG | AAG | ACG | ATA | GCC | 2256 |
| Asn | Pro | Gly | Glu | Val | Arg | Thr | Trp | Val | Lys | Val | Met | Lys | Thr | Ile | Ala |      |
|     |     |     | 740 |     |     |     |     | 745 |     |     |     |     | 750 |     |     |      |
| GTC | GAT | GAG | GAC | ACT | TGG | GAG | GCA | AGA | AGC | AGG | TCA | GGC | TTG | AGG | CAG | 2304 |
| Val | Asp | Glu | Asp | Thr | Trp | Glu | Ala | Arg | Ser | Arg | Ser | Gly | Leu | Arg | Gln |      |
|     |     | 755 |     |     |     |     | 760 |     |     |     |     | 765 |     |     |     |      |
| ATC | GTA | CGA | CGA | AGT | CCT | GAA | AAA | GCT | CAT | ACA | GGC | CTG | GAC | AGG | GTT | 2352 |
| Ile | Val | Arg | Arg | Ser | Pro | Glu | Lys | Ala | His | Thr | Gly | Leu | Asp | Arg | Val |      |
|     | 770 |     |     |     |     | 775 |     |     |     |     | 780 |     |     |     |     |      |
| GAC | TCG | ACA | AGG | CCG | AGA | GCG | GCA | ACG | ACG | AGG | AGG | CCG | AGC | TCA | TGC | 2400 |
| Asp | Ser | Thr | Arg | Pro | Arg | Ala | Ala | Thr | Thr | Arg | Arg | Pro | Ser | Ser | Cys |      |
| 785 |     |     |     |     | 790 |     |     |     |     | 795 |     |     |     |     | 800 |      |
| TCA | ACC | TCA | AGA | ACA | AGA | AGA | CGG | GAG | GAC | AGG | GTA | ATG | AAG | AGA | CTC | 2448 |
| Ser | Thr | Ser | Arg | Thr | Arg | Arg | Arg | Glu | Asp | Arg | Val | Met | Lys | Arg | Leu |      |
|     |     |     |     | 805 |     |     |     |     | 810 |     |     |     |     | 815 |     |      |
| CCT | GAG | AGG | GTC | TCT | TTC | GAT | CCC | GAG | GCG | TTC | GTT | GAG | ATA | AAC | CGA | 2496 |
| Pro | Glu | Arg | Val | Ser | Phe | Asp | Pro | Glu | Ala | Phe | Val | Glu | Ile | Asn | Arg |      |
|     |     |     | 820 |     |     |     |     | 825 |     |     |     |     | 830 |     |     |      |
| AAG | AGA | AAC | AGG | GAC | TTT | TTA | GAG | TTC | CTC | TTG | GCG | GAG | TTC | CAG | GTG | 2544 |
| Lys | Arg | Asn | Arg | Asp | Phe | Leu | Glu | Phe | Leu | Leu | Ala | Glu | Phe | Gln | Val |      |
|     |     | 835 |     |     |     |     | 840 |     |     |     |     | 845 |     |     |     |      |
| NCG | GTT | TCC | TTC | TTC | ACG | GTT | CAT | CCA | TAC | CTC | CTC | GGC | AAG | ACC | TAT | 2592 |
| Xaa | Val | Ser | Phe | Phe | Thr | Val | His | Pro | Tyr | Leu | Leu | Gly | Lys | Thr | Tyr |      |
|     | 850 |     |     |     |     | 855 |     |     |     |     | 860 |     |     |     |     |      |
| CTG | GGC | AGG | GAC | CTG | GAA | AGC | GAA | GTT | CGG | GCC | CTC | AAC | GAA | GCC | TAC | 2640 |
| Leu | Gly | Arg | Asp | Leu | Glu | Ser | Glu | Val | Arg | Ala | Leu | Asn | Glu | Ala | Tyr |      |
| 865 |     |     |     |     | 870 |     |     |     |     | 875 |     |     |     |     | 880 |      |
| ACC | ATC | GTG | TAT | CCC | ACG | AAA | GAA | CTC | CTC | ATG | AGG | GCC | ATA | GAA | ATC | 2688 |
| Thr | Ile | Val | Tyr | Pro | Thr | Lys | Glu | Leu | Leu | Met | Arg | Ala | Ile | Glu | Ile |      |
|     |     |     |     | 885 |     |     |     |     | 890 |     |     |     |     | 895 |     |      |
| GAG | GCG | AGG | CTG | ATA | AAA | AGG | GGA | ATT | TTT | CTC | TCT | TTC | GAC | GAC | ATC | 2736 |
| Glu | Ala | Arg | Leu | Ile | Lys | Arg | Gly | Ile | Phe | Leu | Ser | Phe | Asp | Asp | Ile |      |
|     |     |     | 900 |     |     |     |     | 905 |     |     |     |     | 910 |     |     |      |
| GTC | ATT | GGA | GTA | ACT | GCC | ATT | GAA | AAC | AAC | GCC | CTT | CTC | GTG | AGC | TCT | 2784 |
| Val | Ile | Gly | Val | Thr | Ala | Ile | Glu | Asn | Asn | Ala | Leu | Leu | Val | Ser | Ser |      |
|     |     | 915 |     |     |     |     | 920 |     |     |     |     | 925 |     |     |     |      |
| GCC | CCC | TCA | CGC | TAC | AGG | CCC | CTT | GAG | AAG | TAC | GGG | CTC | AAC | GTT | ATG | 2832 |
| Ala | Pro | Ser | Arg | Tyr | Arg | Pro | Leu | Glu | Lys | Tyr | Gly | Leu | Asn | Val | Met |      |
|     | 930 |     |     |     |     | 935 |     |     |     |     | 940 |     |     |     |     |      |
| GGG | CTC | AAG | CTC | CTT | CTT | CGA | CGA | ACT | CCG | GAA | GCT | CGC | CCG | GAA | GGA | 2880 |
| Gly | Leu | Lys | Leu | Leu | Leu | Arg | Arg | Thr | Pro | Glu | Ala | Arg | Pro | Glu | Gly |      |
| 945 |     |     |     |     | 950 |     |     |     |     | 955 |     |     |     |     | 960 |      |
| AGC | CGC | CAG | ATG | GGA | GGT | GCC | CCC | GGT | GGG | ATC | TTC | TCC | AGA | ACG | AGA | 2928 |
| Ser | Arg | Gln | Met | Gly | Gly | Ala | Pro | Gly | Gly | Ile | Phe | Ser | Arg | Thr | Arg |      |
|     |     |     |     | 965 |     |     |     |     | 970 |     |     |     |     | 975 |     |      |
| ATG | AAC | GCT | ATC | CTC | GGG | AAG | AGC | CAG | CGG | AGG | CTT | CTC | GCC | CTA | AAG | 2976 |
| Met | Asn | Ala | Ile | Leu | Gly | Lys | Ser | Gln | Arg | Arg | Leu | Leu | Ala | Leu | Lys |      |
|     |     |     | 980 |     |     |     |     | 985 |     |     |     |     | 990 |     |     |      |
| CCC | CTC | TCC | TCG | AAC | TCC | CCC | CTA | AGC | TCC | TCC | GGT | GAG | GGA | AAG | GCG | 3024 |
| Pro | Leu | Ser | Ser | Asn | Ser | Pro | Leu | Ser | Ser | Ser | Gly | Glu | Gly | Lys | Ala |      |
|     |     | 995 |     |     |     |     | 1000|     |     |     |     | 1005|     |     |     |      |
| TCT | ATC | GAG | CTG | ACA | AGG | TGT | TCG | GCT | TTC | TCG | TTG | CCC | GTC | GTC | AGC | 3072 |
| Ser | Ile | Glu | Leu | Thr | Arg | Cys | Ser | Ala | Phe | Ser | Leu | Pro | Val | Val | Ser |      |
|     |     | 1010|     |     |     |     | 1015|     |     |     |     | 1020|     |     |     |      |
| TTT | CCG | ATG | AGG | GGA | ACA | ACC | GTT | CTC | GTG | AGC | CAG | GCC | ATC | TTT | CCA | 3120 |
| Phe | Pro | Met | Arg | Gly | Thr | Thr | Val | Leu | Val | Ser | Gln | Ala | Ile | Phe | Pro |      |

| | | | | | | | | | | | | | | | | |
|---|---|---|---|---|---|---|---|---|---|---|---|---|---|---|---|---|
|1025| | | | |1030| | | | |1035| | | | |1040| |
|AGG|AGC|GAG|GGG|TTC|TTT|GAG|AAC|TCG|AGG|ATT|ACG|AGC|CTT|CCT|CCC|3168|
|Arg|Ser|Glu|Gly|Phe|Phe|Glu|Asn|Ser|Arg|Ile|Thr|Ser|Leu|Pro|Pro| |
| | | | |1045| | | | |1050| | | | |1055| | |
|GGC|TTC|AGA|ACA|CGG|TGG|AGC|TCC|TCT|ATA|GCT|TTT|TCC|CTA|TCG|GAG|3216|
|Gly|Phe|Arg|Thr|Arg|Trp|Ser|Ser|Ser|Ile|Ala|Phe|Ser|Leu|Ser|Glu| |
| | | |1060| | | | |1065| | | | |1070| | | |
|AAG|NTT|CTG|AGG|TCG|GAG|GCG|ACG|CTG|ACA|ATG|TCG|NAG|CTC|CCG|TCC|3264|
|Lys|Xaa|Leu|Arg|Ser|Glu|Ala|Thr|Leu|Thr|Met|Ser|Xaa|Leu|Pro|Ser| |
| | |1075| | | | |1080| | | | |1085| | | | |
|GGA|GNC|ATT|TCT|TCC|GCC|CTG|CCA|ACG|CTC|AGC|CTC|GCG|NAG|GGG|ACC|3312|
|Gly|Xaa|Ile|Ser|Ser|Ala|Leu|Pro|Thr|Leu|Ser|Leu|Ala|Xaa|Gly|Thr| |
| | |1090| | | | |1095| | | | |1100| | | | |
|TTT|CTC|CCC|GCT|ATC|CTG|AGC|ATC|TCC|TCG|CTG|CAG|TCG|AGG|CCG|AAC|3360|
|Phe|Leu|Pro|Ala|Ile|Leu|Ser|Ile|Ser|Ser|Leu|Gln|Ser|Arg|Pro|Asn| |
|1105| | | | |1110| | | | |1115| | | | |1120| |
|TAC|GCC|CGA|CAG|GTT|TCT|CTT|TTC|AAG|CCT|CTT|CCT|CAT|GCA|GAG|CAT|3408|
|Tyr|Ala|Arg|Gln|Val|Ser|Leu|Phe|Lys|Pro|Leu|Pro|His|Ala|Glu|His| |
| | | | |1125| | | | |1130| | | | |1135| | |
|CAT|GTC|CCT|GGT|TCC|GCA|GGC|CAC|GTC|AAG|GAT|TTT|CGG|CCT|TTC|GCG|3456|
|His|Val|Pro|Gly|Ser|Ala|Gly|His|Val|Lys|Asp|Phe|Arg|Pro|Phe|Ala| |
| | | |1140| | | | |1145| | | | |1150| | | |
|AAC|CTC|AAG|GGA|CTT|CAA|AAC|CTC|CTC|GCA|GGC|CTT|TTT|CCT|CCA|CAA|3504|
|Asn|Leu|Lys|Gly|Leu|Gln|Asn|Leu|Leu|Ala|Gly|Leu|Phe|Pro|Pro|Gln| |
| | |1155| | | | |1160| | | | |1165| | | | |
|CCT|GTC|GAG|ACT|GAG|GCT|TAT|CAG|CCT|GTT|GGT|ATC|GTA|GCG|CTC|CGC|3552|
|Pro|Val|Glu|Thr|Glu|Ala|Tyr|Gln|Pro|Val|Gly|Ile|Val|Ala|Leu|Arg| |
| | |1170| | | | |1175| | | | |1180| | | | |
|AAT|GCT|GTC|AAA|GAG|CTC|CCT|TAC|CAA|GCT|CCT|CCC|TCC|CGA|GGA|CCT|3600|
|Asn|Ala|Val|Lys|Glu|Leu|Pro|Tyr|Gln|Ala|Pro|Pro|Ser|Arg|Gly|Pro| |
|1185| | | | |1190| | | | |1195| | | | |1200| |
|TCT|TTA|TCT|TCG|CGG|GCC|TTC|CGC|CTA|GGT|AAA|CCC|TGT|CCG|CAA|TTT|3648|
|Ser|Leu|Ser|Ser|Arg|Ala|Phe|Arg|Leu|Gly|Lys|Pro|Cys|Pro|Gln|Phe| |
| | | | |1205| | | | |1210| | | | |1215| | |
|AGA|GCT|CCT|CGA|GCT|GGT|GCG|AGA|CGA|CCA|GAA|CGC|CTT|TTC|CAG|AAT|3696|
|Arg|Ala|Pro|Arg|Ala|Gly|Ala|Arg|Arg|Pro|Glu|Arg|Leu|Phe|Gln|Asn| |
| | | |1220| | | | |1225| | | | |1230| | | |
|TGG|CTA|ATT|CCC|GAA|TTA|TGG|AAA|GAA|GTT|CTT|CTT|TGG|AGC|GCG|CGT|3744|
|Trp|Leu|Ile|Pro|Glu|Leu|Trp|Lys|Glu|Val|Leu|Leu|Trp|Ser|Ala|Arg| |
| | |1235| | | | |1240| | | | |1245| | | | |
|CGA|GGC|CGG|AGG|GCT|CGT|CCA|GAA|TCA|GGA|CAT|CGA|AGT|CCA|GCA|GGG|3792|
|Arg|Gly|Arg|Arg|Ala|Arg|Pro|Glu|Ser|Gly|His|Arg|Ser|Pro|Ala|Gly| |
| |1250| | | | |1255| | | | |1260| | | | | |
|CGC|GCA|GGA|GAG|AAG|TTT|TTC|TCC|TCG|TCC|CCC|CGC|TCA|CTT|CCT|TTG|3840|
|Arg|Ala|Gly|Glu|Lys|Phe|Phe|Ser|Ser|Ser|Pro|Arg|Ser|Leu|Pro|Leu| |
|1265| | | | |1270| | | | |1275| | | | |1280| |
|GAT|AGA|GGT|CGA|GGT|AGT|TCT|CCA|GGC|CGA|GTC|TCT|CCA|CGT|ATT|CGA|3888|
|Asp|Arg|Gly|Arg|Gly|Ser|Ser|Pro|Gly|Arg|Val|Ser|Pro|Arg|Ile|Arg| |
| | | | |1285| | | | |1290| | | | |1295| | |
|GCC|TGC|ACT|CCC|TTC|CCC|AGC|GGG|CCG|GCA|GGC|AGA|CGT|TGT|CCC|GCC|3936|
|Ala|Cys|Thr|Pro|Phe|Pro|Ser|Gly|Pro|Ala|Gly|Arg|Arg|Cys|Pro|Ala| |
| | | |1300| | | | |1305| | | | |1310| | | |
|TCT|TCC|ACG|GCA|GAA|GGT|AGT|CCT|CCT|GAT|AGA|GGA|CGG|AGG|GGT|TCT|3984|
|Ser|Ser|Thr|Ala|Glu|Gly|Ser|Pro|Pro|Asp|Arg|Gly|Arg|Arg|Gly|Ser| |
| | |1315| | | | |1320| | | | |1325| | | | |
|TCA|CAA|AGA|CCT|CGC|CCG|AGT|CCG|GGT|TCT|CAA|CTC|CGG|CCA|AAA|TCT|4032|
|Ser|Gln|Arg|Pro|Arg|Pro|Ser|Pro|Gly|Ser|Gln|Leu|Arg|Pro|Lys|Ser| |
| |1330| | | | |1335| | | | |1340| | | | | |
|TCA|CGA|GGG|TGC|TCT|TTC|CCG|TCC|CGT|TCG|GCC|CGA|GGC|CGA|CCA|CCT|4080|
|Ser|Arg|Gly|Cys|Ser|Phe|Pro|Ser|Arg|Ser|Ala|Arg|Gly|Arg|Pro|Pro| |

```
                                                                             -continued
 1345                          1350                         1355                         1360
 CGC   CGG   CCC   CCT   CAA   GGC   CCC   CGT   CGA   GTA   TGG   GCT   CAC   AGG   ACT   TTC    4128
 Arg   Arg   Pro   Pro   Gln   Gly   Pro   Arg   Arg   Val   Trp   Ala   His   Arg   Thr   Phe
                         1365                         1370                         1375

GGT   TCT   TCA   CCA   GTA   CCA   GCC   TTT   CAC   CCA   TTC   CTC   GAC   CTC   CTC   AGA    4176
 Gly   Ser   Ser   Pro   Val   Pro   Ala   Phe   His   Pro   Phe   Leu   Asp   Leu   Leu   Arg
                   1380                         1385                         1390

AGT   AGC   TGG   TCG   AGG   GTT   ATC   ATG   AGC   AGG   ATT   AAG   AGC   AGT   GCC   CAG    4224
 Ser   Ser   Trp   Ser   Arg   Val   Ile   Met   Ser   Arg   Ile   Lys   Ser   Ser   Ala   Gln
             1395                         1400                         1405

GCA   AAA   ACA   CCG   GCT   TTA   ATT   CCC   AAA   TCG   GAG   ACG   AGC   TGG   CCG   ATT    4272
 Ala   Lys   Thr   Pro   Ala   Leu   Ile   Pro   Lys   Ser   Glu   Thr   Ser   Trp   Pro   Ile
       1410                         1415                         1420

CCT   CCC   GCT   GAA   CCA   AAA   GCC   TCG   GCA   ACG   ACG   CTT   ATC   CTG   AGC   GCT    4320
 Pro   Pro   Ala   Glu   Pro   Lys   Ala   Ser   Ala   Thr   Thr   Leu   Ile   Leu   Ser   Ala
 1425                    1430                         1435                         1440

ATT   CCC   AGG   GCG   ACT   CTG   CCT   GCC   GAG   ACC   ATC   TCG   GGG   AGC   GTT   CCC    4368
 Ile   Pro   Arg   Ala   Thr   Leu   Pro   Ala   Glu   Thr   Ile   Ser   Gly   Ser   Val   Pro
                   1445                         1450                         1455

GGG   ACG   ATG   AAG   TGC   CGG   AGC   AGC   TTT   GAG   GGT   TTG   AGG   AGA   ACT   ATC    4416
 Gly   Thr   Met   Lys   Cys   Arg   Ser   Ser   Phe   Glu   Gly   Leu   Arg   Arg   Thr   Ile
             1460                         1465                         1470

AGC   GGG   CGG   TAT   TTT   TCT   ATC   ACC   TTT   TCG   CTT   GAG   CTC   ACT   CCA   GC     4463
 Ser   Gly   Arg   Tyr   Phe   Ser   Ile   Thr   Phe   Ser   Leu   Glu   Leu   Thr   Pro
       1475                         1480                         1485
```

( 2 ) INFORMATION FOR SEQ ID NO:2:

( i ) SEQUENCE CHARACTERISTICS:
        ( A ) LENGTH: 1487 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
 Asn   Ser   Arg   Met   Asn   Leu   Ile   Trp   Ser   Val   Leu   Ser   Leu   Tyr   Ile   Pro
  1                      5                        10                            15

Glu   Pro   Met   Gly   Phe   Ser   Leu   Leu   Ala   Tyr   Phe   Ile   Gly   Ser   Leu   Met
                    20                       25                          30

Ser   Phe   Gln   Met   Cys   Ser   Gly   Thr   Ile   Gly   Ile   Trp   Ser   Gln   Ser   His
                    35                       40                          45

Ser   Ala   Cys   Gly   Ser   Leu   Lys   Met   Lys   Ser   Thr   Val   Leu   Ser   Ser   Thr
        50                       55                        60

Thr   Leu   Thr   Ser   Leu   Ser   Gln   Pro   Gln   Thr   Leu   Glu   Lys   Glu   Ala   Pro
  65                           70                        75                             80

Val   Trp   Phe   Phe   Ala   Arg   Lys   Val   Asn   Leu   Thr   Ser   Ser   Ala   Val   Arg
                          85                        90                          95

Gly   Phe   Pro   Ser   Cys   Gln   Val   Arg   Pro   Ser   Phe   Ser   Leu   Thr   Ser   Val
                   100                       105                         110

Leu   Ser   Leu   Ile   His   Phe   Pro   Asp   Ser   Ala   Ser   Gln   Gly   Met   Ser   Trp
                   115                       120                         125

Ser   Phe   Ser   Gly   Ser   Lys   Asn   Arg   Gly   Ser   Met   Arg   Leu   Ser   Cys   Leu
             130                       135                         140

Leu   Arg   Pro   Arg   Arg   Gln   Gly   Asp   Ser   Ser   Ser   Ala   Asp   Ser   Thr   Asp
 145                           150                       155                             160

Arg   Leu   Gln   Arg   Arg   Gly   Phe   His   Ser   Trp   Glu   Ala   Pro   Arg   Arg   Gly
                         165                       170                         175
```

```
Arg  Ser  Pro  Arg  Ile  Gln  Gln  Gly  Leu  Lys  Pro  Ser  Ala  Leu  Pro  Ala
               180                 185                      190

Ala  Asn  Gln  Gly  Phe  Val  Ser  Cys  Ala  Pro  Pro  Gln  Thr  Ala  Arg  Val
          195                      200                 205

Cys  Ser  Tyr  Lys  Asn  Ala  Leu  Gln  Ile  Tyr  Lys  Thr  Leu  Gly  Ser  Val
     210                      215                 220

Ile  Lys  Leu  Gly  Gln  Lys  Leu  Lys  Ser  Ala  Asn  Leu  Ile  Arg  Glu  Lys
225                      230                      235                      240

Gly  Lys  Val  Thr  Trp  Gly  Leu  Val  Tyr  Ala  Thr  Arg  Arg  Leu  Ser  Leu
                    245                      250                      255

Gly  Arg  Val  Pro  Val  Arg  Leu  Ser  Val  Arg  Asp  Gly  Arg  Gln  Ala  Gln
               260                 265                      270

Glu  Glu  His  Ser  Glu  His  Arg  Leu  Val  Glu  Val  Gly  Gln  Gly  Ser  Leu
               275                 280                      285

Gln  His  Lys  Glu  Gly  Thr  Arg  Gln  Arg  Arg  Pro  Ala  Arg  Gly  Gly  Asp
          290                      295                 300

Lys  Gln  Leu  Arg  Thr  Leu  Arg  Glu  Gly  Ser  Pro  Pro  Arg  Gln  Arg  Pro
305                      310                      315                      320

Arg  Ser  Glu  Arg  Leu  Gln  Asp  Trp  Asn  Arg  Val  Glu  Gln  Asp  Leu  Ser
                    325                      330                      335

Leu  Ala  Asn  Val  Val  Cys  Gly  Gly  Arg  Ala  Gly  Gln  Leu  Arg  Thr  Arg
               340                 345                      350

Glu  Gly  Arg  Gln  Asn  Arg  Arg  His  Ala  Arg  Arg  Ala  Arg  Arg  Asp  Ser
          355                      360                 365

Glu  Ser  Ser  Gly  Asp  Ser  Leu  Leu  Pro  Pro  Arg  Tyr  Arg  Ala  Pro  Gln
     370                      375                 380

Gly  Ala  Gly  Leu  Gln  Gly  His  Arg  Glu  Pro  Gln  Pro  Leu  His  Ala  Pro
385                      390                      395                      400

Pro  Leu  Ala  Ser  Arg  Ser  Asp  Asn  Arg  Glu  Gly  Glu  Gly  Pro  His  Gln
                    405                      410                      415

Arg  Asp  Trp  Leu  Gly  Arg  Ala  Gly  Glu  Arg  Gly  Gly  Val  Arg  Gln  Val
               420                 425                      430

Arg  Gly  Val  His  Arg  Glu  Arg  Thr  Arg  Gly  Pro  Arg  Tyr  Val  Glu  His
               435                 440                      445

Leu  Gln  Arg  Ala  Asp  Gly  Arg  Cys  Gly  Ala  Arg  Leu  Pro  Arg  Ala  Leu
     450                      455                 460

Leu  Arg  Leu  Ser  Ala  Gly  Gly  Tyr  Glu  Pro  Arg  Gly  Gly  Lys  Ala  Gly
465                      470                      475                      480

Asn  Pro  Gln  His  Asp  Lys  Arg  Pro  Arg  Thr  Gly  Leu  Gln  Asp  Asp  Lys
                    485                      490                      495

Glu  Val  Arg  Gln  Gly  Lys  Gly  Arg  Gly  Phe  Pro  Leu  Arg  Gly  Arg  Gly
               500                 505                      510

Arg  Asp  Asn  Leu  Gln  Gln  His  Arg  Arg  Cys  Leu  Ser  Ile  Arg  Leu  Gln
               515                 520                      525

Arg  Pro  Lys  Gly  Arg  Glu  Ser  Cys  Arg  Lys  Arg  Gln  Leu  Leu  Pro  Gln
          530                      535                 540

Arg  Ala  Leu  Leu  Arg  Arg  Asn  Pro  Gln  Gly  Gln  Ala  Gln  His  Arg  Val
545                      550                      555                      560

Arg  Arg  Asp  Leu  Arg  Gln  Ser  Ser  Ala  Ser  Gln  Gly  Glu  Arg  Leu  Asp
                    565                      570                      575

Arg  Arg  Leu  Leu  His  Glu  Arg  Ser  Arg  Gln  Val  Phe  Gly  Ala  Gln  Val
               580                 585                      590

Pro  Glu  His  Thr  Pro  Asp  Ile  Leu  Pro  Gly  Ser  Ser  Gln  Leu  Arg  Leu
```

|     |     |     | 595 |     |     |     | 600 |     |     |     | 605 |     |     |     |
| --- | --- | --- | --- | --- | --- | --- | --- | --- | --- | --- | --- | --- | --- | --- |

Arg Leu Gln Ala Arg Glu Phe Phe Arg Arg Arg Lys Ala Arg Lys Arg
610                       615                       620

His Arg Leu Gly Asp Leu Ser Gly Gly Asp Leu Arg Leu Asp Lys Arg
625                       630                       635                       640

Gly Gln Gln Ile Arg Gly Pro Gly Leu Arg His Arg Lys Arg Asn Ser
                          645                       650                       655

Arg Phe Asn His Pro Ala Ala Val Leu Pro Arg Glu Pro Cys Ser Glu
            660                       665                       670

Asp Gly Gly Val Arg Gly Gly Leu Arg Arg Gln Gly Leu Pro Leu Leu
            675                       680                       685

Gly Ala Asp Arg Gln Leu Arg Val Gly Pro Arg Phe Gln Asp Glu Val
690                       695                       700

Arg Pro Leu Ser Gly Ser His Asn Gln Gly Glu Asn Thr Ala Gly Gly
705                       710                       715                       720

Lys Arg Lys Gly Leu Gly His Arg Gly Glu Gln Arg Ser Glu Gln Gly
                          725                       730                       735

Asn Pro Gly Glu Val Arg Thr Trp Val Lys Val Met Lys Thr Ile Ala
            740                       745                       750

Val Asp Glu Asp Thr Trp Glu Ala Arg Ser Arg Ser Gly Leu Arg Gln
            755                       760                       765

Ile Val Arg Arg Ser Pro Glu Lys Ala His Thr Gly Leu Asp Arg Val
770                       775                       780

Asp Ser Thr Arg Pro Arg Ala Ala Thr Thr Arg Arg Pro Ser Ser Cys
785                       790                       795                       800

Ser Thr Ser Arg Thr Arg Arg Arg Glu Asp Arg Val Met Lys Arg Leu
                  805                       810                       815

Pro Glu Arg Val Ser Phe Asp Pro Glu Ala Phe Val Glu Ile Asn Arg
            820                       825                       830

Lys Arg Asn Arg Asp Phe Leu Glu Phe Leu Leu Ala Glu Phe Gln Val
            835                       840                       845

Xaa Val Ser Phe Phe Thr Val His Pro Tyr Leu Leu Gly Lys Thr Tyr
    850                       855                       860

Leu Gly Arg Asp Leu Glu Ser Glu Val Arg Ala Leu Asn Glu Ala Tyr
865                       870                       875                       880

Thr Ile Val Tyr Pro Thr Lys Glu Leu Leu Met Arg Ala Ile Glu Ile
                  885                       890                       895

Glu Ala Arg Leu Ile Lys Arg Gly Ile Phe Leu Ser Phe Asp Asp Ile
            900                       905                       910

Val Ile Gly Val Thr Ala Ile Glu Asn Asn Ala Leu Leu Val Ser Ser
            915                       920                       925

Ala Pro Ser Arg Tyr Arg Pro Leu Glu Lys Tyr Gly Leu Asn Val Met
930                       935                       940

Gly Leu Lys Leu Leu Leu Arg Arg Thr Pro Glu Ala Arg Pro Glu Gly
945                       950                       955                       960

Ser Arg Gln Met Gly Gly Ala Pro Gly Gly Ile Phe Ser Arg Thr Arg
                  965                       970                       975

Met Asn Ala Ile Leu Gly Lys Ser Gln Arg Arg Leu Leu Ala Leu Lys
            980                       985                       990

Pro Leu Ser Ser Asn Ser Pro Leu Ser Ser Ser Gly Glu Gly Lys Ala
      995                       1000                      1005

Ser Ile Glu Leu Thr Arg Cys Ser Ala Phe Ser Leu Pro Val Val Ser
      1010                      1015                      1020

```
Phe  Pro  Met  Arg  Gly  Thr  Thr  Val  Leu  Val  Ser  Gln  Ala  Ile  Phe  Pro
1025                 1030                 1035                      1040

Arg  Ser  Glu  Gly  Phe  Phe  Glu  Asn  Ser  Arg  Ile  Thr  Ser  Leu  Pro  Pro
                1045                 1050                 1055

Gly  Phe  Arg  Thr  Arg  Trp  Ser  Ser  Ser  Ile  Ala  Phe  Ser  Leu  Ser  Glu
           1060                 1065                      1070

Lys  Xaa  Leu  Arg  Ser  Glu  Ala  Thr  Leu  Thr  Met  Ser  Xaa  Leu  Pro  Ser
      1075                 1080                      1085

Gly  Xaa  Ile  Ser  Ser  Ala  Leu  Pro  Thr  Leu  Ser  Leu  Ala  Xaa  Gly  Thr
      1090                 1095                      1100

Phe  Leu  Pro  Ala  Ile  Leu  Ser  Ile  Ser  Ser  Leu  Gln  Ser  Arg  Pro  Asn
1105                 1110                 1115                      1120

Tyr  Ala  Arg  Gln  Val  Ser  Leu  Phe  Lys  Pro  Leu  Pro  His  Ala  Glu  His
                1125                 1130                 1135

His  Val  Pro  Gly  Ser  Ala  Gly  His  Val  Lys  Asp  Phe  Arg  Pro  Phe  Ala
           1140                 1145                      1150

Asn  Leu  Lys  Gly  Leu  Gln  Asn  Leu  Leu  Ala  Gly  Leu  Phe  Pro  Pro  Gln
      1155                 1160                      1165

Pro  Val  Glu  Thr  Glu  Ala  Tyr  Gln  Pro  Val  Gly  Ile  Val  Ala  Leu  Arg
      1170                 1175                      1180

Asn  Ala  Val  Lys  Glu  Leu  Pro  Tyr  Gln  Ala  Pro  Pro  Ser  Arg  Gly  Pro
1185                 1190                 1195                      1200

Ser  Leu  Ser  Ser  Arg  Ala  Phe  Arg  Leu  Gly  Lys  Pro  Cys  Pro  Gln  Phe
                1205                 1210                 1215

Arg  Ala  Pro  Arg  Ala  Gly  Ala  Arg  Arg  Pro  Glu  Arg  Leu  Phe  Gln  Asn
           1220                 1225                      1230

Trp  Leu  Ile  Pro  Glu  Leu  Trp  Lys  Glu  Val  Leu  Leu  Trp  Ser  Ala  Arg
      1235                 1240                      1245

Arg  Gly  Arg  Arg  Ala  Arg  Pro  Glu  Ser  Gly  His  Arg  Ser  Pro  Ala  Gly
      1250                 1255                      1260

Arg  Ala  Gly  Glu  Lys  Phe  Phe  Ser  Ser  Pro  Arg  Ser  Leu  Pro  Leu
1265                 1270                 1275                      1280

Asp  Arg  Gly  Arg  Gly  Ser  Ser  Pro  Gly  Arg  Val  Ser  Pro  Arg  Ile  Arg
           1285                 1290                      1295

Ala  Cys  Thr  Pro  Phe  Pro  Ser  Gly  Pro  Ala  Gly  Arg  Arg  Cys  Pro  Ala
           1300                 1305                      1310

Ser  Ser  Thr  Ala  Glu  Gly  Ser  Pro  Pro  Asp  Arg  Gly  Arg  Arg  Gly  Ser
           1315                 1320                      1325

Ser  Gln  Arg  Pro  Arg  Pro  Ser  Pro  Gly  Ser  Gln  Leu  Arg  Pro  Lys  Ser
      1330                 1335                      1340

Ser  Arg  Gly  Cys  Ser  Phe  Pro  Ser  Arg  Ser  Ala  Arg  Gly  Arg  Pro  Pro
1345                 1350                 1355                      1360

Arg  Arg  Pro  Pro  Gln  Gly  Pro  Arg  Arg  Val  Trp  Ala  His  Arg  Thr  Phe
                1365                 1370                 1375

Gly  Ser  Ser  Pro  Val  Pro  Ala  Phe  His  Pro  Phe  Leu  Asp  Leu  Leu  Arg
           1380                 1385                      1390

Ser  Ser  Trp  Ser  Arg  Val  Ile  Met  Ser  Arg  Ile  Lys  Ser  Ser  Ala  Gln
           1395                 1400                      1405

Ala  Lys  Thr  Pro  Ala  Leu  Ile  Pro  Lys  Ser  Glu  Thr  Ser  Trp  Pro  Ile
      1410                 1415                      1420

Pro  Pro  Ala  Glu  Pro  Lys  Ala  Ser  Ala  Thr  Thr  Leu  Ile  Leu  Ser  Ala
1425                 1430                 1435                      1440

Ile  Pro  Arg  Ala  Thr  Leu  Pro  Ala  Glu  Thr  Ile  Ser  Gly  Ser  Val  Pro
           1445                 1450                      1455
```

-continued

```
Gly  Thr  Met  Lys  Cys  Arg  Ser  Ser  Phe  Glu  Gly  Leu  Arg  Arg  Thr  Ile
              1460                    1465                    1470
Ser  Gly  Arg  Tyr  Phe  Ser  Ile  Thr  Phe  Ser  Leu  Glu  Leu  Thr  Pro
         1475                    1480                    1485
```

(2) INFORMATION FOR SEQ ID NO:3:

(i) SEQUENCE CHARACTERISTICS:
        (A) LENGTH: 4463 base pairs
        (B) TYPE: nucleic acid
        (C) STRANDEDNESS: single
        (D) TOPOLOGY: linear (ii) MOLECULE TYPE: Genomic DNA (ix) FEATURE:
        (A) NAME/KEY: Coding Sequence
        (B) LOCATION: 1...4461

(xi) SEQUENCE DESCRIPTION: SEQ ID NO:3:

```
AAT  TCC  AGG  ATG  AAC  CTC  ATC  TGG  TCG  GTC  TTG  AGC  TTG  TAC  ATT  CCG        48
Asn  Ser  Arg  Met  Asn  Leu  Ile  Trp  Ser  Val  Leu  Ser  Leu  Tyr  Ile  Pro
 1                    5                   10                   15

GAA  CCG  ATG  GGG  TTC  TCG  CTG  TTG  GCG  TAC  TTT  ATC  GGG  TCT  TTG  ATG        96
Glu  Pro  Met  Gly  Phe  Ser  Leu  Leu  Ala  Tyr  Phe  Ile  Gly  Ser  Leu  Met
                20                        25                        30

TCC  TTC  CAG  ATG  TGC  TCA  GGG  ACG  ATC  GGG  ATC  TGG  AGC  CAG  TCC  CAC       144
Ser  Phe  Gln  Met  Cys  Ser  Gly  Thr  Ile  Gly  Ile  Trp  Ser  Gln  Ser  His
          35                        40                        45

TCC  GCG  TGC  GGA  TCG  CTG  AAG  ATG  AAA  TCA  ACG  GTT  CTG  TCG  TCA  ACG       192
Ser  Ala  Cys  Gly  Ser  Leu  Lys  Met  Lys  Ser  Thr  Val  Leu  Ser  Ser  Thr
     50                        55                        60

ACC  TTG  ACC  TCC  TTG  AGC  CAG  CCC  CAA  ACG  CTC  GAG  AAG  GAG  GCA  CCG       240
Thr  Leu  Thr  Ser  Leu  Ser  Gln  Pro  Gln  Thr  Leu  Glu  Lys  Glu  Ala  Pro
 65                       70                        75                        80

GTG  TGG  TTC  TTC  GCG  AGG  AAG  GTG  AAC  TTA  ACG  TCT  TCA  GCG  GTT  AGG       288
Val  Trp  Phe  Phe  Ala  Arg  Lys  Val  Asn  Leu  Thr  Ser  Ser  Ala  Val  Arg
                     85                        90                        95

GGC  TTT  CCG  TCC  TGC  CAG  GTT  AGG  CCC  TCC  TTC  AGC  TTG  ACC  TCG  GTG       336
Gly  Phe  Pro  Ser  Cys  Gln  Val  Arg  Pro  Ser  Phe  Ser  Leu  Thr  Ser  Val
               100                       105                       110

TTG  TCG  TTG  ATC  CAC  TTC  CCA  GAC  TCG  GCC  AGC  CAG  GGA  ATG  AGC  TGG       384
Leu  Ser  Leu  Ile  His  Phe  Pro  Asp  Ser  Ala  Ser  Gln  Gly  Met  Ser  Trp
          115                       120                       125

TCC  TTC  AGC  GGG  TCG  AAG  AAC  AGG  GGC  TCG  ATG  AGG  CTA  TCG  TGC  CTG       432
Ser  Phe  Ser  Gly  Ser  Lys  Asn  Arg  Gly  Ser  Met  Arg  Leu  Ser  Cys  Leu
     130                       135                       140

CTG  CGG  CCC  AGG  AGA  CAA  GGG  GAT  AGT  TCG  TCG  GCT  GAC  TCC  ACA  GAC       480
Leu  Arg  Pro  Arg  Arg  Gln  Gly  Asp  Ser  Ser  Ser  Ala  Asp  Ser  Thr  Asp
145                      150                       155                       160

CGC  CTC  CAA  CGT  AGA  GGG  TTT  CAT  TCC  TGG  GAA  GCT  CCT  CGG  CGC  GGA       528
Arg  Leu  Gln  Arg  Arg  Gly  Phe  His  Ser  Trp  Glu  Ala  Pro  Arg  Arg  Gly
                    165                       170                       175

CGT  AGC  CCG  CGA  ATC  CAA  CAA  GGC  TTG  AAA  CCA  TCA  GCA  CTG  CCA  GCA       576
Arg  Ser  Pro  Arg  Ile  Gln  Gln  Gly  Leu  Lys  Pro  Ser  Ala  Leu  Pro  Ala
               180                       185                       190

GCA  AAC  CAA  GGA  TTC  GTC  TCA  TGC  GCA  CCA  CCC  CAG  ACC  GCG  AGG  GTC       624
Ala  Asn  Gln  Gly  Phe  Val  Ser  Cys  Ala  Pro  Pro  Gln  Thr  Ala  Arg  Val
          195                       200                       205

TGT  AGT  TAT  AAA  AAC  GCG  CTC  CAA  ATT  TAT  AAA  ACT  TTG  GGT  TCT  GTT       672
Cys  Ser  Tyr  Lys  Asn  Ala  Leu  Gln  Ile  Tyr  Lys  Thr  Leu  Gly  Ser  Val
     210                       215                       220
```

| | | | | | | | | | | | | | | | | |
|---|---|---|---|---|---|---|---|---|---|---|---|---|---|---|---|---|
| ATA | AAA | TTG | GGG | CAA | AAA | TTA | AAA | TCG | GCA | AAC | CTT | ATA | AGG | GAG | AAA | 720 |
| Ile | Lys | Leu | Gly | Gln | Lys | Leu | Lys | Ser | Ala | Asn | Leu | Ile | Arg | Glu | Lys | |
| 225 | | | | 230 | | | | 235 | | | | | | | 240 | |
| GGC | AAA | GTT | ACA | TGG | GGG | TTG | GTC | TAT | GCT | ACC | AGA | AGG | CTT | TCT | CTG | 768 |
| Gly | Lys | Val | Thr | Trp | Gly | Leu | Val | Tyr | Ala | Thr | Arg | Arg | Leu | Ser | Leu | |
| | | | 245 | | | | | 250 | | | | | | 255 | | |
| GGG | CGT | GTC | CCA | GTC | CGG | CTT | TCA | GTT | CGA | GAT | GGG | CGA | CAA | GCT | CAG | 816 |
| Gly | Arg | Val | Pro | Val | Arg | Leu | Ser | Val | Arg | Asp | Gly | Arg | Gln | Ala | Gln | |
| | | | 260 | | | | | 265 | | | | | 270 | | | |
| GAG | GAA | CAT | TCC | GAA | CAC | AGA | CTG | GTG | GAA | GTG | GGT | CAG | GGA | TCC | CTT | 864 |
| Glu | Glu | His | Ser | Glu | His | Arg | Leu | Val | Glu | Val | Gly | Gln | Gly | Ser | Leu | |
| | | | 275 | | | | 280 | | | | | 285 | | | | |
| CAA | CAT | AAA | GAG | GGA | ACT | CGT | CAG | CGG | CGA | CCT | GCC | CGA | GGA | GGG | GAT | 912 |
| Gln | His | Lys | Glu | Gly | Thr | Arg | Gln | Arg | Arg | Pro | Ala | Arg | Gly | Gly | Asp | |
| | 290 | | | | | 295 | | | | | 300 | | | | | |
| AAA | CAA | CTA | CGA | ACT | TTA | CGA | GAA | GGA | TCA | CCG | CCT | CGC | CAG | AGA | CCT | 960 |
| Lys | Gln | Leu | Arg | Thr | Leu | Arg | Glu | Gly | Ser | Pro | Pro | Arg | Gln | Arg | Pro | |
| 305 | | | | 310 | | | | | 315 | | | | | | 320 | |
| CGG | TCT | GAA | CGT | TTA | CAG | GAT | TGG | AAT | AGA | GTG | GAG | CAG | GAT | CTT | TCC | 1008 |
| Arg | Ser | Glu | Arg | Leu | Gln | Asp | Trp | Asn | Arg | Val | Glu | Gln | Asp | Leu | Ser | |
| | | | | 325 | | | | 330 | | | | | 335 | | | |
| CTG | GCC | AAC | GTG | GTT | TGT | GGA | GGT | CGT | GCG | GGA | CAG | CTA | CGG | ACT | CGT | 1056 |
| Leu | Ala | Asn | Val | Val | Cys | Gly | Gly | Arg | Ala | Gly | Gln | Leu | Arg | Thr | Arg | |
| | | | 340 | | | | | 345 | | | | | 350 | | | |
| GAA | GGA | CGT | CAA | AAT | CGA | AGA | CAC | GCT | CGA | AGA | GCT | CGA | CGA | GAT | AGC | 1104 |
| Glu | Gly | Arg | Gln | Asn | Arg | Arg | His | Ala | Arg | Arg | Ala | Arg | Arg | Asp | Ser | |
| | | 355 | | | | | 360 | | | | | 365 | | | | |
| GAA | TCA | TCA | GGA | GAT | AGC | CTA | CTA | CCG | CCG | CGT | TAT | AGA | GCA | CCT | CAG | 1152 |
| Glu | Ser | Ser | Gly | Asp | Ser | Leu | Leu | Pro | Pro | Arg | Tyr | Arg | Ala | Pro | Gln | |
| | 370 | | | | | 375 | | | | | 380 | | | | | |
| GGA | GCT | GGG | CTT | CAA | GGT | CAT | CGT | GAA | CCT | CAA | CCA | CTT | CAC | GCT | CCC | 1200 |
| Gly | Ala | Gly | Leu | Gln | Gly | His | Arg | Glu | Pro | Gln | Pro | Leu | His | Ala | Pro | |
| 385 | | | | | 390 | | | | | 395 | | | | | 400 | |
| CCT | CTG | GCT | TCA | CGA | TCC | GAT | AAT | CGC | GAG | GGA | GAA | GGC | CCT | CAC | CAA | 1248 |
| Pro | Leu | Ala | Ser | Arg | Ser | Asp | Asn | Arg | Glu | Gly | Glu | Gly | Pro | His | Gln | |
| | | | | 405 | | | | | 410 | | | | | 415 | | |
| CGG | GAT | TGG | CTG | GGT | CGG | GCA | GGA | GAG | CGT | GGT | GGA | GTT | CGC | CAA | GTA | 1296 |
| Arg | Asp | Trp | Leu | Gly | Arg | Ala | Gly | Glu | Arg | Gly | Gly | Val | Arg | Gln | Val | |
| | | | 420 | | | | | 425 | | | | | 430 | | | |
| CGC | GGC | GTA | CAT | CGC | GAA | CGC | ACT | CGG | GGA | CCT | CGT | TAT | GTG | GAG | CAC | 1344 |
| Arg | Gly | Val | His | Arg | Glu | Arg | Thr | Arg | Gly | Pro | Arg | Tyr | Val | Glu | His | |
| | | 435 | | | | | 440 | | | | | 445 | | | | |
| CTT | CAA | CGA | GCC | GAT | GGT | CGT | TGT | GGA | GCT | CGG | TTA | CCT | CGC | GCC | CTA | 1392 |
| Leu | Gln | Arg | Ala | Asp | Gly | Arg | Cys | Gly | Ala | Arg | Leu | Pro | Arg | Ala | Leu | |
| | 450 | | | | | 455 | | | | | 460 | | | | | |
| CTC | CGG | CTT | TCC | GCC | GGG | GGT | TAT | GAA | CCC | CGA | GGC | GGC | AAA | GCT | GGC | 1440 |
| Leu | Arg | Leu | Ser | Ala | Gly | Gly | Tyr | Glu | Pro | Arg | Gly | Gly | Lys | Ala | Gly | |
| 465 | | | | | 470 | | | | | 475 | | | | | 480 | |
| AAT | CCT | CAA | CAT | GAT | AAA | CGC | CCA | CGC | ACT | GGC | CTA | CAA | GAT | GAT | AAA | 1488 |
| Asn | Pro | Gln | His | Asp | Lys | Arg | Pro | Arg | Thr | Gly | Leu | Gln | Asp | Asp | Lys | |
| | | | 485 | | | | | 490 | | | | | 495 | | | |
| GAA | GTT | CGA | CAG | GGT | AAA | GGC | CGA | GGA | TTC | CCG | CTC | AGG | CGA | GGT | | 1536 |
| Glu | Val | Arg | Gln | Gly | Lys | Gly | Arg | Gly | Phe | Pro | Leu | Arg | Gly | Arg | Gly | |
| | | | 500 | | | | | 505 | | | | | 510 | | | |
| CGG | GAT | AAT | CTA | CAA | CAA | CAT | AGG | CGT | TGC | CTA | TCC | ATA | CGA | CTC | CAA | 1584 |
| Arg | Asp | Asn | Leu | Gln | Gln | His | Arg | Arg | Cys | Leu | Ser | Ile | Arg | Leu | Gln | |
| | | 515 | | | | | 520 | | | | | 525 | | | | |
| CGA | CCC | AAA | GGA | CGT | GAA | AGC | TGC | AGA | AAA | CGA | CAA | CTA | CTT | CCA | CAG | 1632 |
| Arg | Pro | Lys | Gly | Arg | Glu | Ser | Cys | Arg | Lys | Arg | Gln | Leu | Leu | Pro | Gln | |
| | 530 | | | | | 535 | | | | | 540 | | | | | |

| | | | | | | | | | | | | | | | | |
|---|---|---|---|---|---|---|---|---|---|---|---|---|---|---|---|---|
| CGG | GCT | CTT | CTT | CGA | CGC | AAT | CCA | CAA | GGG | CAA | GCT | CAA | CAT | CGA | GTT | 1680 |
| Arg | Ala | Leu | Leu | Arg | Arg | Asn | Pro | Gln | Gly | Gln | Ala | Gln | His | Arg | Val | |
| 545 | | | | 550 | | | | | 555 | | | | | | 560 | |
| CGA | CGG | GAC | CTT | CGT | CAA | AGT | TCG | GCA | TCT | CAG | GGG | GAA | CGA | CTG | GAT | 1728 |
| Arg | Arg | Asp | Leu | Arg | Gln | Ser | Ser | Ala | Ser | Gln | Gly | Glu | Arg | Leu | Asp | |
| | | | | 565 | | | | | 570 | | | | | | 575 | |
| AGG | CGT | CTA | CTA | CAC | GAG | AGA | AGT | CGT | CAG | GTA | TTC | GGA | GCC | CAA | GTT | 1776 |
| Arg | Arg | Leu | Leu | His | Glu | Arg | Ser | Arg | Gln | Val | Phe | Gly | Ala | Gln | Val | |
| | | | | 580 | | | | | 585 | | | | | | 590 | |
| CCC | GAG | CAT | ACC | CCT | GAT | ATC | CTT | CCG | GGG | AGT | TCA | CAA | CTA | CGG | CTA | 1824 |
| Pro | Glu | His | Thr | Pro | Asp | Ile | Leu | Pro | Gly | Ser | Ser | Gln | Leu | Arg | Leu | |
| | | 595 | | | | | 600 | | | | | 605 | | | | |
| CGC | CTG | CAG | GCC | CGG | GAG | TTC | TTC | CGC | CGA | CGG | AAG | GCC | CGT | AAG | CGA | 1872 |
| Arg | Leu | Gln | Ala | Arg | Glu | Phe | Phe | Arg | Arg | Arg | Lys | Ala | Arg | Lys | Arg | |
| | 610 | | | | | 615 | | | | | 620 | | | | | |
| CAT | CGG | CTG | GGA | GAT | CTA | TCC | GGA | GGG | GAT | CTA | CGA | CTC | GAT | AAG | AGA | 1920 |
| His | Arg | Leu | Gly | Asp | Leu | Ser | Gly | Gly | Asp | Leu | Arg | Leu | Asp | Lys | Arg | |
| 625 | | | | 630 | | | | | 635 | | | | | | 640 | |
| GGC | CAA | CAA | ATA | CGG | GGT | CCC | GGT | TTA | CGT | CAC | CGA | AAA | CGG | AAT | AGC | 1968 |
| Gly | Gln | Gln | Ile | Arg | Gly | Pro | Gly | Leu | Arg | His | Arg | Lys | Arg | Asn | Ser | |
| | | | | 645 | | | | | 650 | | | | | | 655 | |
| CGA | TTC | AAC | CAC | CCT | GCG | GCC | GTA | CTA | CCT | CGC | GAG | CCA | TGT | AGC | GAA | 2016 |
| Arg | Phe | Asn | His | Pro | Ala | Ala | Val | Leu | Pro | Arg | Glu | Pro | Cys | Ser | Glu | |
| | | | 660 | | | | | 665 | | | | | 670 | | | |
| GAT | GGA | GGC | GTA | CGA | GGC | GGG | TTA | CGA | CGT | CAG | GGG | CTA | CCT | CTA | CTG | 2064 |
| Asp | Gly | Gly | Val | Arg | Gly | Gly | Leu | Arg | Arg | Gln | Gly | Leu | Pro | Leu | Leu | |
| | | 675 | | | | | 680 | | | | | 685 | | | | |
| GGC | GCT | GAC | CGA | CAA | CTA | CGA | GTG | GGC | CCT | CGG | TTT | CAG | GAT | GAG | GTT | 2112 |
| Gly | Ala | Asp | Arg | Gln | Leu | Arg | Val | Gly | Pro | Arg | Phe | Gln | Asp | Glu | Val | |
| | | 690 | | | | | 695 | | | | | 700 | | | | |
| CGG | CCT | CTA | AGT | GGA | TCT | CAT | AAC | CAA | GGA | GAG | AAC | ACC | GCG | GGA | GGA | 2160 |
| Arg | Pro | Leu | Ser | Gly | Ser | His | Asn | Gln | Gly | Glu | Asn | Thr | Ala | Gly | Gly | |
| 705 | | | | | 710 | | | | | 715 | | | | | 720 | |
| AAG | CGT | AAA | GGT | TTA | GGG | CAT | CGT | GGA | GAA | CAA | CGG | AGT | GAG | CAA | GGA | 2208 |
| Lys | Arg | Lys | Gly | Leu | Gly | His | Arg | Gly | Glu | Gln | Arg | Ser | Glu | Gln | Gly | |
| | | | | 725 | | | | | 730 | | | | | | 735 | |
| AAT | CCG | GGA | GAA | GTT | CGG | ACT | TGG | GTG | AAG | GTA | ATG | AAG | ACG | ATA | GCC | 2256 |
| Asn | Pro | Gly | Glu | Val | Arg | Thr | Trp | Val | Lys | Val | Met | Lys | Thr | Ile | Ala | |
| | | | 740 | | | | | 745 | | | | | 750 | | | |
| GTC | GAT | GAG | GAC | ACT | TGG | GAG | GCA | AGA | AGC | AGG | TCA | GGC | TTG | AGG | CAG | 2304 |
| Val | Asp | Glu | Asp | Thr | Trp | Glu | Ala | Arg | Ser | Arg | Ser | Gly | Leu | Arg | Gln | |
| | | 755 | | | | | 760 | | | | | 765 | | | | |
| ATC | GTA | CGA | CGA | AGT | CCT | GAA | AAA | GCT | CAT | ACA | GGC | CTG | GAC | AGG | GTT | 2352 |
| Ile | Val | Arg | Arg | Ser | Pro | Glu | Lys | Ala | His | Thr | Gly | Leu | Asp | Arg | Val | |
| | 770 | | | | | 775 | | | | | 780 | | | | | |
| GAC | TCG | ACA | AGG | CCG | AGA | GCG | GCA | ACG | ACG | AGG | CCG | AGC | TCA | TGC | 2400 |
| Asp | Ser | Thr | Arg | Pro | Arg | Ala | Ala | Thr | Thr | Arg | Arg | Pro | Ser | Ser | Cys | |
| 785 | | | | | 790 | | | | | 795 | | | | | 800 | |
| TCA | ACC | TCA | AGA | ACA | AGA | AGA | CGG | GAG | GAC | AGG | GTA | ATG | AAG | AGA | CTC | 2448 |
| Ser | Thr | Ser | Arg | Thr | Arg | Arg | Arg | Glu | Asp | Arg | Val | Met | Lys | Arg | Leu | |
| | | | | 805 | | | | | 810 | | | | | | 815 | |
| CCT | GAG | AGG | GTC | TCT | TTC | GAT | CCC | GAG | GCG | TTC | GTT | GAG | ATA | AAC | CGA | 2496 |
| Pro | Glu | Arg | Val | Ser | Phe | Asp | Pro | Glu | Ala | Phe | Val | Glu | Ile | Asn | Arg | |
| | | | 820 | | | | | 825 | | | | | 830 | | | |
| AAG | AGA | AAC | AGG | GAC | TTT | TTA | GAG | TTC | CTC | TTG | GCG | GAG | TTC | CAG | GTG | 2544 |
| Lys | Arg | Asn | Arg | Asp | Phe | Leu | Glu | Phe | Leu | Leu | Ala | Glu | Phe | Gln | Val | |
| | | 835 | | | | | 840 | | | | | 845 | | | | |
| NCG | GTT | TCC | TTC | TTC | ACG | GTT | CAT | CCA | TAC | CTC | CTC | GGC | AAG | ACC | TAT | 2592 |
| Xaa | Val | Ser | Phe | Phe | Thr | Val | His | Pro | Tyr | Leu | Leu | Gly | Lys | Thr | Tyr | |
| 850 | | | | | 855 | | | | | 860 | | | | | | |

| | | | | | | | | | | | | | | | | |
|---|---|---|---|---|---|---|---|---|---|---|---|---|---|---|---|---|
| CTG | GGC | AGG | GAC | CTG | GAA | AGC | GAA | GTT | CGG | GCC | CTC | AAC | GAA | GCC | TAC | 2640 |
| Leu | Gly | Arg | Asp | Leu | Glu | Ser | Glu | Val | Arg | Ala | Leu | Asn | Glu | Ala | Tyr | |
| 865 | | | | 870 | | | | 875 | | | | | | | 880 | |
| ACC | ATC | GTG | TAT | CCC | ACG | AAA | GAA | CTC | CTC | ATG | AGG | GCC | ATA | GAA | ATC | 2688 |
| Thr | Ile | Val | Tyr | Pro | Thr | Lys | Glu | Leu | Leu | Met | Arg | Ala | Ile | Glu | Ile | |
| | | | | 885 | | | | | 890 | | | | | | 895 | |
| GAG | GCG | AGG | CTG | ATA | AAA | AGG | GGA | ATT | TTT | CTC | TCT | TTC | GAC | GAC | ATC | 2736 |
| Glu | Ala | Arg | Leu | Ile | Lys | Arg | Gly | Ile | Phe | Leu | Ser | Phe | Asp | Asp | Ile | |
| | | | 900 | | | | | 905 | | | | | 910 | | | |
| GTC | ATT | GGA | GTA | ACT | GCC | ATT | GAA | AAC | AAC | GCC | CTT | CTC | GTG | AGC | TCT | 2784 |
| Val | Ile | Gly | Val | Thr | Ala | Ile | Glu | Asn | Asn | Ala | Leu | Leu | Val | Ser | Ser | |
| | | 915 | | | | | 920 | | | | | 925 | | | | |
| GCC | CCC | TCA | CGC | TAC | AGG | CCC | CTT | GAG | AAG | TAC | GGG | CTC | AAC | GTT | ATG | 2832 |
| Ala | Pro | Ser | Arg | Tyr | Arg | Pro | Leu | Glu | Lys | Tyr | Gly | Leu | Asn | Val | Met | |
| | 930 | | | | | 935 | | | | | 940 | | | | | |
| GGG | CTC | AAG | CTC | CTT | CTT | CGA | CGA | ACT | CCG | GAA | GCT | CGC | CCG | GAA | GGA | 2880 |
| Gly | Leu | Lys | Leu | Leu | Leu | Arg | Arg | Thr | Pro | Glu | Ala | Arg | Pro | Glu | Gly | |
| 945 | | | | 950 | | | | 955 | | | | | | 960 | | |
| AGC | CGC | CAG | ATG | GGA | GGT | GCC | CCC | GGT | GGG | ATC | TTC | TCC | AGA | ACG | AGA | 2928 |
| Ser | Arg | Gln | Met | Gly | Gly | Ala | Pro | Gly | Gly | Ile | Phe | Ser | Arg | Thr | Arg | |
| | | | | 965 | | | | | 970 | | | | | 975 | | |
| ATG | AAC | GCT | ATC | CTC | GGG | AAG | AGC | CAG | CGG | AGG | CTT | CTC | GCC | CTA | AAG | 2976 |
| Met | Asn | Ala | Ile | Leu | Gly | Lys | Ser | Gln | Arg | Arg | Leu | Leu | Ala | Leu | Lys | |
| | | | 980 | | | | | 985 | | | | | 990 | | | |
| CCC | CTC | TCC | TCG | AAC | TCC | CCC | CTA | AGC | TCC | TCC | GGT | GAG | GGA | AAG | GCG | 3024 |
| Pro | Leu | Ser | Ser | Asn | Ser | Pro | Leu | Ser | Ser | Ser | Gly | Glu | Gly | Lys | Ala | |
| | | 995 | | | | | 1000 | | | | | 1005 | | | | |
| TCT | ATC | GAG | CTG | ACA | AGG | TGT | TCG | GCT | TTC | TCG | TTG | CCC | GTC | GTC | AGC | 3072 |
| Ser | Ile | Glu | Leu | Thr | Arg | Cys | Ser | Ala | Phe | Ser | Leu | Pro | Val | Val | Ser | |
| | 1010 | | | | | 1015 | | | | | 1020 | | | | | |
| TTT | CCG | ATG | AGG | GGA | ACA | ACC | GTT | CTC | GTG | AGC | CAG | GCC | ATC | TTT | CCA | 3120 |
| Phe | Pro | Met | Arg | Gly | Thr | Thr | Val | Leu | Val | Ser | Gln | Ala | Ile | Phe | Pro | |
| 1025 | | | | 1030 | | | | 1035 | | | | | | 1040 | | |
| AGG | AGC | GAG | GGG | TTC | TTT | GAG | AAC | TCG | AGG | ATT | ACG | AGC | CTT | CCT | CCC | 3168 |
| Arg | Ser | Glu | Gly | Phe | Phe | Glu | Asn | Ser | Arg | Ile | Thr | Ser | Leu | Pro | Pro | |
| | | | | 1045 | | | | | 1050 | | | | | 1055 | | |
| GGC | TTC | AGA | ACA | CGG | TGG | AGC | TCC | TCT | ATA | GCT | TTT | TCC | CTA | TCG | GAG | 3216 |
| Gly | Phe | Arg | Thr | Arg | Trp | Ser | Ser | Ser | Ile | Ala | Phe | Ser | Leu | Ser | Glu | |
| | | | 1060 | | | | | 1065 | | | | | 1070 | | | |
| AAG | NTT | CTG | AGG | TCG | GAG | GCG | ACG | CTG | ACA | ATG | TCG | NAG | CTC | CCG | TCC | 3264 |
| Lys | Xaa | Leu | Arg | Ser | Glu | Ala | Thr | Leu | Thr | Met | Ser | Xaa | Leu | Pro | Ser | |
| | | 1075 | | | | | 1080 | | | | | 1085 | | | | |
| GGA | GNC | ATT | TCT | TCC | GCC | CTG | CCA | ACG | CTC | AGC | CTC | GCG | NAG | GGG | ACC | 3312 |
| Gly | Xaa | Ile | Ser | Ser | Ala | Leu | Pro | Thr | Leu | Ser | Leu | Ala | Xaa | Gly | Thr | |
| | 1090 | | | | | 1095 | | | | | 1100 | | | | | |
| TTT | CTC | CCC | GCT | ATC | CTG | AGC | ATC | TCC | TCG | CTG | CAG | TCG | AGG | CCG | AAC | 3360 |
| Phe | Leu | Pro | Ala | Ile | Leu | Ser | Ile | Ser | Ser | Leu | Gln | Ser | Arg | Pro | Asn | |
| 1105 | | | | 1110 | | | | | 1115 | | | | | 1120 | | |
| TAC | GCC | CGA | CAG | GTT | TCT | CTT | TTC | AAG | CCT | CTT | CCT | CAT | GCA | GAG | CAT | 3408 |
| Tyr | Ala | Arg | Gln | Val | Ser | Leu | Phe | Lys | Pro | Leu | Pro | His | Ala | Glu | His | |
| | | | 1125 | | | | | 1130 | | | | | 1135 | | | |
| CAT | GTC | CCT | GGT | TCC | GCA | GGC | CAC | GTC | AAG | GAT | TTT | CGG | CCT | TTC | GCG | 3456 |
| His | Val | Pro | Gly | Ser | Ala | Gly | His | Val | Lys | Asp | Phe | Arg | Pro | Phe | Ala | |
| | | | 1140 | | | | | 1145 | | | | | 1150 | | | |
| AAC | CTC | AAG | GGA | CTT | CAA | AAC | CTC | CTC | GCA | GGC | CTT | TTT | CCT | CCA | CAA | 3504 |
| Asn | Leu | Lys | Gly | Leu | Gln | Asn | Leu | Leu | Ala | Gly | Leu | Phe | Pro | Pro | Gln | |
| | | 1155 | | | | | 1160 | | | | | 1165 | | | | |
| CCT | GTC | GAG | ACT | GAG | GCT | TAT | CAG | CCT | GTT | GGT | ATC | GTA | GCG | CTC | CGC | 3552 |
| Pro | Val | Glu | Thr | Glu | Ala | Tyr | Gln | Pro | Val | Gly | Ile | Val | Ala | Leu | Arg | |
| | 1170 | | | | | 1175 | | | | | 1180 | | | | | |

```
AAT GCT GTC AAA GAG CTC CCT TAC CAA GCT CCT CCC TCC CGA GGA CCT      3600
Asn Ala Val Lys Glu Leu Pro Tyr Gln Ala Pro Pro Ser Arg Gly Pro
1185                1190                1195                1200

TCT TTA TCT TCG CGG GCC TTC CGC CTA GGT AAA CCC TGT CCG CAA TTT      3648
Ser Leu Ser Ser Arg Ala Phe Arg Leu Gly Lys Pro Cys Pro Gln Phe
        1205                1210                1215

AGA GCT CCT CGA GCT GGT GCG AGA CGA CCA GAA CGC CTT TTC CAG AAT      3696
Arg Ala Pro Arg Ala Gly Ala Arg Arg Pro Glu Arg Leu Phe Gln Asn
            1220                1225                1230

TGG CTA ATT CCC GAA TTA TGG AAA GAA GTT CTT CTT TGG AGC GCG CGT      3744
Trp Leu Ile Pro Glu Leu Trp Lys Glu Val Leu Leu Trp Ser Ala Arg
        1235                1240                1245

CGA GGC CGG AGG GCT CGT CCA GAA TCA GGA CAT CGA AGT CCA GCA GGG      3792
Arg Gly Arg Arg Ala Arg Pro Glu Ser Gly His Arg Ser Pro Ala Gly
    1250                1255                1260

CGC GCA GGA GAG AAG TTT TTC TCC TCG TCC CCC CGC TCA CTT CCT TTG      3840
Arg Ala Gly Glu Lys Phe Phe Ser Ser Ser Pro Arg Ser Leu Pro Leu
1265                1270                1275                1280

GAT AGA GGT CGA GGT AGT TCT CCA GGC CGA GTC TCT CCA CGT ATT CGA      3888
Asp Arg Gly Arg Gly Ser Ser Pro Gly Arg Val Ser Pro Arg Ile Arg
        1285                1290                1295

GCC TGC ACT CCC TTC CCC AGC GGG CCG GCA GGC AGA CGT TGT CCC GCC      3936
Ala Cys Thr Pro Phe Pro Ser Gly Pro Ala Gly Arg Arg Cys Pro Ala
            1300                1305                1310

TCT TCC ACG GCA GAA GGT AGT CCT CCT GAT AGA GGA CGG AGG GGT TCT      3984
Ser Ser Thr Ala Glu Gly Ser Pro Pro Asp Arg Gly Arg Arg Gly Ser
        1315                1320                1325

TCA CAA AGA CCT CGC CCG AGT CCG GGT TCT CAA CTC CGG CCA AAA TCT      4032
Ser Gln Arg Pro Arg Pro Ser Pro Gly Ser Gln Leu Arg Pro Lys Ser
    1330                1335                1340

TCA CGA GGG TGC TCT TTC CCG TCC CGT TCG GCC CGA GGC CGA CCA CCT      4080
Ser Arg Gly Cys Ser Phe Pro Ser Arg Ser Ala Arg Gly Arg Pro Pro
1345                1350                1355                1360

CGC CGG CCC CCT CAA GGC CCC CGT CGA GTA TGG GCT CAC AGG ACT TTC      4128
Arg Arg Pro Pro Gln Gly Pro Arg Arg Val Trp Ala His Arg Thr Phe
        1365                1370                1375

GGT TCT TCA CCA GTA CCA GCC TTT CAC CCA TTC CTC GAC CTC CTC AGA      4176
Gly Ser Ser Pro Val Pro Ala Phe His Pro Phe Leu Asp Leu Leu Arg
            1380                1385                1390

AGT AGC TGG TCG AGG GTT ATC ATG AGC AGG ATT AAG AGC AGT GCC CAG      4224
Ser Ser Trp Ser Arg Val Ile Met Ser Arg Ile Lys Ser Ser Ala Gln
        1395                1400                1405

GCA AAA ACA CCG GCT TTA ATT CCC AAA TCG GAG ACG AGC TGG CCG ATT      4272
Ala Lys Thr Pro Ala Leu Ile Pro Lys Ser Glu Thr Ser Trp Pro Ile
    1410                1415                1420

CCT CCC GCT GAA CCA AAA GCC TCG GCA ACG ACG CTT ATC CTG AGC GCT      4320
Pro Pro Ala Glu Pro Lys Ala Ser Ala Thr Thr Leu Ile Leu Ser Ala
1425                1430                1435                1440

ATT CCC AGG GCG ACT CTG CCT GCC GAG ACC ATC TCG GGA GCC GTT CCC      4368
Ile Pro Arg Ala Thr Leu Pro Ala Glu Thr Ile Ser Gly Ser Val Pro
        1445                1450                1455

GGG ACG ATG AAG TGC CGG AGC AGC TTT GAG GGT TTG AGG AGA ACT ATC      4416
Gly Thr Met Lys Cys Arg Ser Ser Phe Glu Gly Leu Arg Arg Thr Ile
            1460                1465                1470

AGC GGG CGG TAT TTT TCT ATC ACC TTT TCG CTT GAG CTC ACT CCA GC       4463
Ser Gly Arg Tyr Phe Ser Ile Thr Phe Ser Leu Glu Leu Thr Pro
        1475                1480                1485
```

( 2 ) INFORMATION FOR SEQ ID NO:4:

( i ) SEQUENCE CHARACTERISTICS:

(A) LENGTH: 1487 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO:4:

| Asn | Ser | Arg | Met | Asn | Leu | Ile | Trp | Ser | Val | Leu | Ser | Leu | Tyr | Ile | Pro |
|---|---|---|---|---|---|---|---|---|---|---|---|---|---|---|---|
| 1 | | | | 5 | | | | | 10 | | | | | 15 | |
| Glu | Pro | Met | Gly | Phe | Ser | Leu | Leu | Ala | Tyr | Phe | Ile | Gly | Ser | Leu | Met |
| | | | 20 | | | | | 25 | | | | | 30 | | |
| Ser | Phe | Gln | Met | Cys | Ser | Gly | Thr | Ile | Gly | Ile | Trp | Ser | Gln | Ser | His |
| | | | 35 | | | | 40 | | | | | 45 | | | |
| Ser | Ala | Cys | Gly | Ser | Leu | Lys | Met | Lys | Ser | Thr | Val | Leu | Ser | Ser | Thr |
| | 50 | | | | | 55 | | | | | 60 | | | | |
| Thr | Leu | Thr | Ser | Leu | Ser | Gln | Pro | Gln | Thr | Leu | Glu | Lys | Glu | Ala | Pro |
| 65 | | | | | 70 | | | | 75 | | | | | | 80 |
| Val | Trp | Phe | Phe | Ala | Arg | Lys | Val | Asn | Leu | Thr | Ser | Ser | Ala | Val | Arg |
| | | | | 85 | | | | | 90 | | | | | 95 | |
| Gly | Phe | Pro | Ser | Cys | Gln | Val | Arg | Pro | Ser | Phe | Ser | Leu | Thr | Ser | Val |
| | | | 100 | | | | | 105 | | | | | 110 | | |
| Leu | Ser | Leu | Ile | His | Phe | Pro | Asp | Ser | Ala | Ser | Gln | Gly | Met | Ser | Trp |
| | | | 115 | | | | | 120 | | | | | 125 | | |
| Ser | Phe | Ser | Gly | Ser | Lys | Asn | Arg | Gly | Ser | Met | Arg | Leu | Ser | Cys | Leu |
| | | | 130 | | | | 135 | | | | | 140 | | | |
| Leu | Arg | Pro | Arg | Arg | Gln | Gly | Asp | Ser | Ser | Ser | Ala | Asp | Ser | Thr | Asp |
| 145 | | | | | | 150 | | | | | 155 | | | | 160 |
| Arg | Leu | Gln | Arg | Arg | Gly | Phe | His | Ser | Trp | Glu | Ala | Pro | Arg | Arg | Gly |
| | | | | 165 | | | | | 170 | | | | | 175 | |
| Arg | Ser | Pro | Arg | Ile | Gln | Gln | Gly | Leu | Lys | Pro | Ser | Ala | Leu | Pro | Ala |
| | | | | 180 | | | | | 185 | | | | | 190 | |
| Ala | Asn | Gln | Gly | Phe | Val | Ser | Cys | Ala | Pro | Pro | Gln | Thr | Ala | Arg | Val |
| | | | 195 | | | | | 200 | | | | | 205 | | |
| Cys | Ser | Tyr | Lys | Asn | Ala | Leu | Gln | Ile | Tyr | Lys | Thr | Leu | Gly | Ser | Val |
| | | | 210 | | | | | 215 | | | | | 220 | | |
| Ile | Lys | Leu | Gly | Gln | Lys | Leu | Lys | Ser | Ala | Asn | Leu | Ile | Arg | Glu | Lys |
| 225 | | | | | 230 | | | | | 235 | | | | | 240 |
| Gly | Lys | Val | Thr | Trp | Gly | Leu | Val | Tyr | Ala | Thr | Arg | Arg | Leu | Ser | Leu |
| | | | | 245 | | | | | 250 | | | | | 255 | |
| Gly | Arg | Val | Pro | Val | Arg | Leu | Ser | Val | Arg | Asp | Gly | Arg | Gln | Ala | Gln |
| | | | 260 | | | | | 265 | | | | | 270 | | |
| Glu | Glu | His | Ser | Glu | His | Arg | Leu | Val | Glu | Val | Gly | Gln | Gly | Ser | Leu |
| | | 275 | | | | | 280 | | | | | 285 | | | |
| Gln | His | Lys | Glu | Gly | Thr | Arg | Gln | Arg | Arg | Pro | Ala | Arg | Gly | Gly | Asp |
| | 290 | | | | | 295 | | | | | 300 | | | | |
| Lys | Gln | Leu | Arg | Thr | Leu | Arg | Glu | Gly | Ser | Pro | Pro | Arg | Gln | Arg | Pro |
| 305 | | | | | 310 | | | | | 315 | | | | | 320 |
| Arg | Ser | Glu | Arg | Leu | Gln | Asp | Trp | Asn | Arg | Val | Glu | Gln | Asp | Leu | Ser |
| | | | | 325 | | | | | 330 | | | | | 335 | |
| Leu | Ala | Asn | Val | Val | Cys | Gly | Gly | Arg | Ala | Gly | Gln | Leu | Arg | Thr | Arg |
| | | | 340 | | | | | 345 | | | | | 350 | | |
| Glu | Gly | Arg | Gln | Asn | Arg | Arg | His | Ala | Arg | Arg | Ala | Arg | Arg | Asp | Ser |
| | | 355 | | | | | 360 | | | | | 365 | | | |
| Glu | Ser | Ser | Gly | Asp | Ser | Leu | Leu | Pro | Pro | Arg | Tyr | Arg | Ala | Pro | Gln |

|     | 370 |     |     |     | 375 |     |     |     | 380 |     |     |
| --- | --- | --- | --- | --- | --- | --- | --- | --- | --- | --- | --- |

Gly Ala Gly Leu Gln Gly His Arg Glu Pro Gln Pro Leu His Ala Pro
385                 390                 395                 400

Pro Leu Ala Ser Arg Ser Asp Asn Arg Glu Gly Glu Gly Pro His Gln
            405                 410                 415

Arg Asp Trp Leu Gly Arg Ala Gly Glu Arg Gly Gly Val Arg Gln Val
        420                 425                 430

Arg Gly Val His Arg Glu Arg Thr Arg Gly Pro Arg Tyr Val Glu His
    435                 440                 445

Leu Gln Arg Ala Asp Gly Arg Cys Gly Ala Arg Leu Pro Arg Ala Leu
450                 455                 460

Leu Arg Leu Ser Ala Gly Gly Tyr Glu Pro Arg Gly Gly Lys Ala Gly
465                 470                 475                 480

Asn Pro Gln His Asp Lys Arg Pro Arg Thr Gly Leu Gln Asp Asp Lys
            485                 490                 495

Glu Val Arg Gln Gly Lys Gly Arg Gly Phe Pro Leu Arg Gly Arg Gly
        500                 505                 510

Arg Asp Asn Leu Gln Gln His Arg Arg Cys Leu Ser Ile Arg Leu Gln
    515                 520                 525

Arg Pro Lys Gly Arg Glu Ser Cys Arg Lys Arg Gln Leu Leu Pro Gln
530                 535                 540

Arg Ala Leu Leu Arg Arg Asn Pro Gln Gly Gln Ala Gln His Arg Val
545                 550                 555                 560

Arg Arg Asp Leu Arg Gln Ser Ser Ala Ser Gln Gly Glu Arg Leu Asp
            565                 570                 575

Arg Arg Leu Leu His Glu Arg Ser Arg Gln Val Phe Gly Ala Gln Val
        580                 585                 590

Pro Glu His Thr Pro Asp Ile Leu Pro Gly Ser Ser Gln Leu Arg Leu
    595                 600                 605

Arg Leu Gln Ala Arg Glu Phe Phe Arg Arg Arg Lys Ala Arg Lys Arg
610                 615                 620

His Arg Leu Gly Asp Leu Ser Gly Gly Asp Leu Arg Leu Asp Lys Arg
625                 630                 635                 640

Gly Gln Gln Ile Arg Gly Pro Gly Leu Arg His Arg Lys Arg Asn Ser
            645                 650                 655

Arg Phe Asn His Pro Ala Ala Val Leu Pro Arg Glu Pro Cys Ser Glu
        660                 665                 670

Asp Gly Gly Val Arg Gly Gly Leu Arg Arg Gln Gly Leu Pro Leu Leu
    675                 680                 685

Gly Ala Asp Arg Gln Leu Arg Val Gly Pro Arg Phe Gln Asp Glu Val
690                 695                 700

Arg Pro Leu Ser Gly Ser His Asn Gln Gly Glu Asn Thr Ala Gly Gly
705                 710                 715                 720

Lys Arg Lys Gly Leu Gly His Arg Gly Glu Gln Arg Ser Glu Gln Gly
            725                 730                 735

Asn Pro Gly Glu Val Arg Thr Trp Val Lys Val Met Lys Thr Ile Ala
        740                 745                 750

Val Asp Glu Asp Thr Trp Glu Ala Arg Ser Arg Ser Gly Leu Arg Gln
    755                 760                 765

Ile Val Arg Arg Ser Pro Glu Lys Ala His Thr Gly Leu Asp Arg Val
770                 775                 780

Asp Ser Thr Arg Pro Arg Ala Ala Thr Thr Arg Arg Pro Ser Ser Cys
785                 790                 795                 800

-continued

```
Ser  Thr  Ser  Arg  Thr  Arg  Arg  Arg  Glu  Asp  Arg  Val  Met  Lys  Arg  Leu
               805                      810                      815

Pro  Glu  Arg  Val  Ser  Phe  Asp  Pro  Glu  Ala  Phe  Val  Glu  Ile  Asn  Arg
               820                      825                      830

Lys  Arg  Asn  Arg  Asp  Phe  Leu  Glu  Phe  Leu  Leu  Ala  Phe  Gln  Val
          835                      840                      845

Xaa  Val  Ser  Phe  Phe  Thr  Val  His  Pro  Tyr  Leu  Leu  Gly  Lys  Thr  Tyr
850                           855                      860

Leu  Gly  Arg  Asp  Leu  Glu  Ser  Glu  Val  Arg  Ala  Leu  Asn  Glu  Ala  Tyr
865                      870                      875                      880

Thr  Ile  Val  Tyr  Pro  Thr  Lys  Glu  Leu  Leu  Met  Arg  Ala  Ile  Glu  Ile
                    885                      890                      895

Glu  Ala  Arg  Leu  Ile  Lys  Arg  Gly  Ile  Phe  Leu  Ser  Phe  Asp  Asp  Ile
               900                      905                      910

Val  Ile  Gly  Val  Thr  Ala  Ile  Glu  Asn  Asn  Ala  Leu  Leu  Val  Ser  Ser
          915                      920                      925

Ala  Pro  Ser  Arg  Tyr  Arg  Pro  Leu  Glu  Lys  Tyr  Gly  Leu  Asn  Val  Met
     930                      935                      940

Gly  Leu  Lys  Leu  Leu  Leu  Arg  Arg  Thr  Pro  Glu  Ala  Arg  Pro  Glu  Gly
945                      950                      955                      960

Ser  Arg  Gln  Met  Gly  Gly  Ala  Pro  Gly  Gly  Ile  Phe  Ser  Arg  Thr  Arg
               965                      970                      975

Met  Asn  Ala  Ile  Leu  Gly  Lys  Ser  Gln  Arg  Arg  Leu  Leu  Ala  Leu  Lys
               980                      985                      990

Pro  Leu  Ser  Ser  Asn  Ser  Pro  Leu  Ser  Ser  Ser  Gly  Glu  Gly  Lys  Ala
          995                      1000                     1005

Ser  Ile  Glu  Leu  Thr  Arg  Cys  Ser  Ala  Phe  Ser  Leu  Pro  Val  Val  Ser
     1010                     1015                     1020

Phe  Pro  Met  Arg  Gly  Thr  Thr  Val  Leu  Val  Ser  Gln  Ala  Ile  Phe  Pro
1025                     1030                     1035                     1040

Arg  Ser  Glu  Gly  Phe  Phe  Glu  Asn  Ser  Arg  Ile  Thr  Ser  Leu  Pro  Pro
               1045                     1050                     1055

Gly  Phe  Arg  Thr  Arg  Trp  Ser  Ser  Ser  Ile  Ala  Phe  Ser  Leu  Ser  Glu
               1060                     1065                     1070

Lys  Xaa  Leu  Arg  Ser  Glu  Ala  Thr  Leu  Thr  Met  Ser  Xaa  Leu  Pro  Ser
     1075                     1080                     1085

Gly  Xaa  Ile  Ser  Ser  Ala  Leu  Pro  Thr  Leu  Ser  Leu  Ala  Xaa  Gly  Thr
     1090                     1095                     1100

Phe  Leu  Pro  Ala  Ile  Leu  Ser  Ile  Ser  Ser  Leu  Gln  Ser  Arg  Pro  Asn
1105                     1110                     1115                     1120

Tyr  Ala  Arg  Gln  Val  Ser  Leu  Phe  Lys  Pro  Leu  Pro  His  Ala  Glu  His
                    1125                     1130                     1135

His  Val  Pro  Gly  Ser  Ala  Gly  His  Val  Lys  Asp  Phe  Arg  Pro  Phe  Ala
               1140                     1145                     1150

Asn  Leu  Lys  Gly  Leu  Gln  Asn  Leu  Leu  Ala  Gly  Leu  Phe  Pro  Pro  Gln
          1155                     1160                     1165

Pro  Val  Glu  Thr  Glu  Ala  Tyr  Gln  Pro  Val  Gly  Ile  Val  Ala  Leu  Arg
     1170                     1175                     1180

Asn  Ala  Val  Lys  Glu  Leu  Pro  Tyr  Gln  Ala  Pro  Pro  Ser  Arg  Gly  Pro
1185                     1190                     1195                     1200

Ser  Leu  Ser  Ser  Arg  Ala  Phe  Arg  Leu  Gly  Lys  Pro  Cys  Pro  Gln  Phe
               1205                     1210                     1215

Arg  Ala  Pro  Arg  Ala  Gly  Ala  Arg  Arg  Pro  Glu  Arg  Leu  Phe  Gln  Asn
               1220                     1225                     1230
```

```
Trp Leu Ile Pro Glu Leu Trp Lys Glu Val Leu Leu Trp Ser Ala Arg
        1235            1240                1245

Arg Gly Arg Arg Ala Arg Pro Glu Ser Gly His Arg Ser Pro Ala Gly
    1250            1255            1260

Arg Ala Gly Glu Lys Phe Phe Ser Ser Ser Pro Arg Ser Leu Pro Leu
1265            1270            1275                    1280

Asp Arg Gly Arg Gly Ser Ser Pro Gly Arg Val Ser Pro Arg Ile Arg
            1285            1290                    1295

Ala Cys Thr Pro Phe Pro Ser Gly Pro Ala Gly Arg Arg Cys Pro Ala
        1300            1305                1310

Ser Ser Thr Ala Glu Gly Ser Pro Pro Asp Arg Gly Arg Arg Gly Ser
        1315            1320                1325

Ser Gln Arg Pro Arg Pro Ser Pro Gly Ser Gln Leu Arg Pro Lys Ser
    1330            1335                1340

Ser Arg Gly Cys Ser Phe Pro Ser Arg Ser Ala Arg Gly Arg Pro Pro
1345            1350                1355                1360

Arg Arg Pro Pro Gln Gly Pro Arg Arg Val Trp Ala His Arg Thr Phe
            1365            1370                1375

Gly Ser Ser Pro Val Pro Ala Phe His Pro Phe Leu Asp Leu Leu Arg
        1380            1385                1390

Ser Ser Trp Ser Arg Val Ile Met Ser Arg Ile Lys Ser Ala Gln
        1395            1400                1405

Ala Lys Thr Pro Ala Leu Ile Pro Lys Ser Glu Thr Ser Trp Pro Ile
    1410            1415                1420

Pro Pro Ala Glu Pro Lys Ala Ser Ala Thr Thr Leu Ile Leu Ser Ala
1425            1430                1435                    1440

Ile Pro Arg Ala Thr Leu Pro Ala Glu Thr Ile Ser Gly Ser Val Pro
            1445            1450                    1455

Gly Thr Met Lys Cys Arg Ser Ser Phe Glu Gly Leu Arg Arg Thr Ile
            1460            1465                1470

Ser Gly Arg Tyr Phe Ser Ile Thr Phe Ser Leu Glu Leu Thr Pro
        1475            1480                1485
```